US011388922B2

(12) United States Patent
Acheson et al.

(10) Patent No.: US 11,388,922 B2
(45) Date of Patent: Jul. 19, 2022

(54) INFANT NUTRITION DELIVERING METABOLIC BENEFITS

(71) Applicant: NESTEC S.A., Vevey (CH)

(72) Inventors: Kevin John Acheson, Kuala Terengganu (MY); Catherine Mace, La Conversion (CH); Yassaman Shahkhalili Dulloo, La Tour de Peilz (CH)

(73) Assignee: Societe des Produits Nestle S.A., Vevey (CH)

( * ) Notice: Subject to any disclaimer, the term of this patent is extended or adjusted under 35 U.S.C. 154(b) by 444 days.

(21) Appl. No.: 16/092,277

(22) PCT Filed: Apr. 10, 2017

(86) PCT No.: PCT/EP2017/058481
§ 371 (c)(1),
(2) Date: Oct. 9, 2018

(87) PCT Pub. No.: WO2017/178395
PCT Pub. Date: Oct. 19, 2017

(65) Prior Publication Data
US 2020/0345054 A1 Nov. 5, 2020

(30) Foreign Application Priority Data

Apr. 11, 2016 (EP) ..................................... 16164763
Apr. 22, 2016 (EP) ..................................... 16166722
May 2, 2016 (EP) ..................................... 16167945

(51) Int. Cl.
*A23L 33/00* (2016.01)
*A23L 7/10* (2016.01)
(Continued)

(52) U.S. Cl.
CPC ............... *A23L 33/40* (2016.08); *A23L 7/198* (2016.08); *A23L 33/105* (2016.08);
(Continued)

(58) Field of Classification Search
CPC .......... A23L 33/40; A23L 7/198; A23L 33/19; A23L 33/22; A23L 33/105; A23L 33/115; A23L 33/125
(Continued)

(56) References Cited

U.S. PATENT DOCUMENTS

2007/0099869 A1* 5/2007 Oku .......................... A23L 5/00
514/61
2011/0244055 A1* 10/2011 Forbes .................... A61K 45/06
424/606
(Continued)

FOREIGN PATENT DOCUMENTS

CN        1809287 A      7/2006
DE    202006006049 U1    8/2006
(Continued)

OTHER PUBLICATIONS

Shahkhalili et al. "Comparison of two models of intrauterine growth restriction for early catch-up growth and later development of glucose intolerance and obesity in rats" Am J Physiol Regul Integr Comp Physiol, Jan. 2010, vol. 298, pp. R141-R146.
(Continued)

*Primary Examiner* — Brent T O'Hern
(74) *Attorney, Agent, or Firm* — K&L Gates LLP

(57) ABSTRACT

The present invention relates to a complementary nutritional composition characterized by a low glycemic load and/or index and/or comprising an ingredient characterized by a low glycemic index for use in treatment, prevention and/or reducing the risk of a metabolic syndrome disorder appearing later in life.

18 Claims, 6 Drawing Sheets

(51) Int. Cl.
*A23L 33/19* (2016.01)
*A23L 33/22* (2016.01)
*A23L 33/105* (2016.01)
*A23L 33/115* (2016.01)
*A23L 33/125* (2016.01)

(52) U.S. Cl.
CPC ........... *A23L 33/115* (2016.08); *A23L 33/125* (2016.08); *A23L 33/19* (2016.08); *A23L 33/22* (2016.08)

(58) Field of Classification Search
USPC .......................................................... 426/661
See application file for complete search history.

(56) References Cited

U.S. PATENT DOCUMENTS

| | | | |
|---|---|---|---|
| 2012/0121757 | A1 | 5/2012 | Zwijsen et al. |
| 2013/0236596 | A1 | 9/2013 | Klassen et al. |
| 2013/0280378 | A1 | 10/2013 | Aichinger et al. |
| 2014/0147551 | A1 | 5/2014 | Roger et al. |
| 2014/0234475 | A1 | 8/2014 | Alles |
| 2014/0286909 | A1 * | 9/2014 | Garcia-Rodenas ........................ A61K 31/202 424/93.4 |
| 2017/0027216 | A1 | 2/2017 | Stahl et al. |

FOREIGN PATENT DOCUMENTS

| | | | |
|---|---|---|---|
| EP | 2474239 | | 7/2012 |
| RU | 2575200 | C2 | 2/2016 |
| WO | 0211562 | A2 | 2/2002 |
| WO | WO-2004112491 | A2 * | 12/2004 ............. A23G 3/48 |
| WO | 2008054208 | A2 | 5/2008 |
| WO | 2008071667 | A1 | 6/2008 |
| WO | 2010066569 | A1 | 6/2010 |
| WO | 2012065809 | A1 | 5/2012 |
| WO | 2012065810 | A1 | 5/2012 |
| WO | WO-2012076057 | A1 * | 6/2012 ............. A23L 33/22 |
| WO | 2013109367 | A1 | 7/2013 |
| WO | WO-2015067761 | A * | 5/2015 ............. A23L 7/143 |
| WO | 2015078505 | A1 | 6/2015 |
| WO | 2015078938 | A1 | 6/2015 |
| WO | 2015078974 | | 6/2015 |
| WO | 2016171571 | A1 | 10/2016 |

OTHER PUBLICATIONS

Srinivasan et al. "A high-carbohydrate diet in the immediate postnatal life of rats induces adaptations predisposing to adult-onset obesity" Journal of Endocrinology, 2008, vol. 197, pp. 565-574.
Pongjanta et al., "Enzymes-Resistant Starch (RS III) from Pullulanase-Debranched High Amylose Rice Starch", Nature Science, vol. 42, Issue No. 5, 2008, pp. 198-205.
Bjorck et al., "Low Glycaemic-Index Foods", British Journal of Nutrition, vol. 83, Issue No. 1, 2000, pp. S149-S155.
Blasetti et al., "Role of Nutrition in Preventing Insulin Resistance in Children", Journal of Pediatric Endocrinology and Metabolism, vol. 29, Issue No. 3, 2016, pp. 247-257.
McKeown et al., "Carbohydrate Nutrition, Insulin Resistance, and the Prevalence of the Metabolic Syndrome in the Framingham Offspring Cohort", Diabetes Care, vol. 27, Issue No. 2, Feb. 2004, pp. 538-546.
Alvisi et al., "Recommendations on Complementary Feeding for Healthy, Full-Term Infants", Italian Journal of Pediatrics, vol. 41, Issue No. 36, 2015, pp. 1-9.
"Maltodextrin",—Wikipedia, Nov. 11, 2021, 3 Pages.
Kabir et al., "A High Glycemic Index Starch Diet Affects Lipid Storage-Related Enzymes in Normal and to a Lesser Extent in Diabetic Rat", The Journal of Nutrition, vol. 128, Issue No. 11, 1998, pp. 1878-1883.
Lerer-Meizger et al., "Effects of Long-Term Low-Glycaemic Index Starchy Food on Plasma Glucose and Lipid Concentrations and Adipose Tissue Cellularity in Normal and Diabetic Rats", British Journal of Nutrition, vol. 75, 1996, pp. 723-732.
Pawlak et al.,"High Glycemic Index Starch Promotes Hypersecretion of Insulin and Higher Body Fat in Rats without Affecting Insulin Sensitivity", The Journal of Nutrition, vol. 131, 2001, pp. 99-104.
Aktinson et al.,"International Tables of Glycemic Index and Glycemic Load Values 2021", 2021, pp. 1-139.
Wright et al.,"Effects of Human Milk and Formula on Postprandial Glycaemia and Insulinaemia", European Journal of Clinical Nutrition, vol. 69, Mar. 25, 2015, pp. 939-943.
"Skimmed Milk Powder—Carbs, Glycemic Index, Fats, Minerals, Vitamins & much more", LowCarb Check, Nov. 8, 2021, pp. 1-7.
"Corn Starch—Carbs, Glycemic Index, Fats, Minerals, Vitamins & much more", LowCarb Check, Nov. 9, 2021, pp. 1-8.
Streit, "What's the Difference Between Corn Flour and Cornstarch?", Healthline, Jul. 4, 2019, pp. 1-17.
Miller et al.,"Effect of Added Carbohydrates on Glycemic and Insulin Responses to Children's Milk Products", Nutrients, vol. 5, 2013, pp. 22-31.
Speith et al., "A Low-Glycemic Index Diet in the Treatment of Pediatric Obesity", Archives of Pediatrics and Adolescent Medicine, vol. 154, 2000, pp. 947-951.
Thompkinson et al., "Aspects of Infant Food Formulation", Comprehensive Reviews in Food Science and Food Safety, vol. 6, Issue No. 4, 2007, pp. 79-102.
McKevith, "Nutritional Aspects of Cereals", Nutrition Bulletin, vol. 29, 2004, 111-142.
Ludwig, "The Glycemic Index: Physiological Mechanisms Relating to Obesity, Diabetes, and Cardiovascular Disease", JAMA, vol. 287, Issue No. 18, May 8, 2002, pp. 2414-2423.
European Patent Office Communication for Application No. 17718037.9-1105, dated Nov. 18, 2021, 50 pages.
Buyken et al., "Optimal Dietary Approaches for Prevention of Type 2 Diabetes: a Life-Course Perspective", Diabetologia, vol. 53, 2010, pp. 406-418, XP19776353.
Ludwig, "Symposium: Dietary Composition and Obestiy: Do We Need To Look Beyond Dietary Fat?", Dietary Glycemic Index and Obesity, Journal of Nutrition, vol. 130, Feb. 2000, pp. 280S-283S, XP002205464.
Russia Patent Office Communication for Application No. 2018139541/10(065633), dated Feb. 22, 2022, 8 pages.

\* cited by examiner

INFANT NUTRITION DELIVERING METABOLIC BENEFITS

CROSS REFERENCE TO RELATED APPLICATIONS

The present application is a National Stage of International Application No. PCT/EP2017/058481, filed on Apr. 10, 2017, which claims priority to European Patent Application No. 16164763.1, filed on Apr. 11, 2016, European Patent Application No. 16166722.5, filed on Apr. 22, 2016, and European Patent Application No. 16167945.1, filed on May 2, 2016, the entire contents of which are being incorporated herein by reference.

TECHNICAL FIELD OF THE INVENTION

The present invention relates to a nutritional composition for the complementary feeding period for use in treatment, prevention and/or reducing the risk of a metabolic syndrome disorder appearing later in life.

BACKGROUND OF THE INVENTION

Data from observational studies suggest that postprandial glycaemia is implicated in development of obesity and chronic metabolic disease such as type 2-diabetes and cardiovascular disease in adults. High/prolonged insulin response is also known to be linked to insulin resistance and risk of type 2 diabetes in adults.

Although extensive data is available on the glycemic index (GI) of different foods and the potential health impact for adults, especially diabetics, much less is known for infant/children, especially healthy.

The prenatal and early postnatal periods are currently recognized as critical windows for early programming. It is now recognized that suboptimal nutrition during critical periods of development may induce long-term alterations in organ structures or functions, which can predispose humans to later chronic diseases.

In particular, evidence exists that prenatal and early postnatal nutrition (lactation) plays a role in determining susceptibility to develop one or more metabolic syndrome disorders later in life (see for example Srinivasan M. et al, "A high carbohydrate diet in the immediate postnatal life of rats induces adaptations predisposing to adult-onset obesity" Journal of endocrinology (2008), 197, 565-574). Anyway, very little is known in relation to the long term metabolic effect of foods intended for complementary feeding period and later feeding of young children (<3 years of age).

Hence, a nutritional composition for administration during the complementary feeding period, which reduces the risk for development of metabolic syndrome disorders later in life would be advantageous.

There is a particular need for specific nutritional compositions that may be administered at particular intervention windows during the early life of the young children and which may be capable to reduce the risk, prevent, or reduce the severity of sub-optimal health conditions usually associated with metabolic syndromes, such as over-weight, obesity, diabetes or even cardiovascular diseases.

There is an even particular need in these infants at higher risk to develop such sub-optimal conditions, for example because of their genetic heritage, of the health conditions of their parents, of their difficult early development.

There is also a need for nutritional compositions to be administered at particular intervention windows during the early life of the young children wherein macronutrients present in the composition would be optimized towards latest nutritional recommendations.

Hence in one embodiment, a nutritional composition for administration during the complementary feeding period which is nutritionally balanced and which reduces the risk for development of metabolic syndrome disorders later in life would be advantageous.

SUMMARY OF THE INVENTION

The present inventors have surprisingly shown that rats which were fed during the complementary feeding period with a diet characterized by a low glycemic index and low glycemic load experienced a protective effect against the impairment of glucose homeostasis and insulin response, even when exposed to an adipogenic diet as adult rats. In contrast, rats which had been fed during the complementary feeding period a diet with higher glycemic index and glycemic load as pups were not protected.

Accordingly, a first aspect of the present invention relates to a complementary nutritional composition characterized by a low glycemic load and/or index for use in treatment, prevention and/or reducing the risk of a metabolic syndrome disorder appearing later in life.

The invention also provides a method of treating, preventing, and/or reducing the risk that an infant or young child will develop a metabolic syndrome disorder later in life; in particular when challenged with adipogenic diet, said method comprising the step of administering at an age of the infant or young children comprised between 4 months and 5 year, a nutritional composition characterized by a low glycaemic load and/or index.

In another aspect, the present invention provides a complementary nutritional composition comprising at least one ingredient having low glycemic index for use in treatment, prevention and/or reducing the risk of a metabolic syndrome disorder appearing later in life.

In another aspect, the present invention provides a complementary nutritional composition comprising at least one carbohydrate-based ingredient having low glycemic index for use in treatment, prevention and/or reducing the risk of a metabolic syndrome disorder appearing later in life.

Another aspect of the present invention relates to the use of at least one carbohydrate-based ingredient having low glycemic index for the preparation of a complementary nutritional composition for use in treatment, prevention or reducing the risk of a metabolic syndrome disorder later in life in an individual.

In a further aspect, the present invention provides for the use of a complementary nutritional composition as described herein for treating, preventing and/or reducing the risk of a metabolic syndrome disorder appearing later in life.

The invention also provides a method of treating, preventing, and/or reducing the risk that an infant or young child will develop a metabolic syndrome disorder later in life; in particular when challenged with adipogenic diet, said method comprising the step of administering at an age of the infant or young children comprised between 4 months and 5 year, a nutritional composition comprising at least ingredient, for example at least one carbohydrate based ingredient, having low glycaemic load and/or index.

In a further aspect, the present invention provides a complementary nutritional set which comprises a complementary nutritional composition characterized by a low glycaemic load and/or index and/or comprising an ingredient with low glycaemic index for use in treatment, prevention and/or reducing the risk of a metabolic syndrome disorder appearing later in life.

In another aspect, the present invention provides a complementary nutritional composition comprising:
- cereal flour in amount ranging from 20 to 90% w/w;
- sugar in amount ranging from 0 to 30% w/w, for example from 0 to 20% w/w, for example between 5 to 18% w/w;
- added sugar with low glycemic index in amount ranging from 0 to 30% w/w, for example from 1 to 20% w/w, for example from 5 to 15% w/w;
- total amount of dietary fiber in amount ranging from 0 to 25% w/w, for example from 2 to 25% w/w;
- added fiber in amount ranging from 0 to 20% w/w;
- legume in amount ranging from 0 to 40%, for example from 1 to 40%, for example, from 5 to 40% w/w;
- fruit in an amount ranging from 0 to 25% w/w, for example from 1 to 18% w/w.

In another aspect, the present invention provides a complementary nutritional composition comprising:
- cereal flour in amount ranging from 20 to 90% w/w, for example from 30 to 55% w/w;
- sugar in amount ranging from 0 to 30% w/w, for example from 0 to 20% w/w, for example between 5 to 18% w/w;
- added sugar with low glycemic index in amount ranging from 0 to 30% w/w, for example from 1 to 20% w/w, for example from 5 to 15% w/w;
- fats in an amount ranging from 8 to 20% w/w of the composition, for example ranging from 10 to 17% w/w, for example from 10 to 15% w/w;
- total amount of dietary fiber in amount ranging from 0 to 25% w/w, for example from 2 to 25% w/w;
- added fiber in amount ranging from 0 to 20% w/w;
- milk-based ingredient in an amount ranging from 0 to 30% w/w, for example from 1 to 25% w/w, for example from 5 to 25% w/w;
- legume in amount ranging from 0 to 40%, for example from 1 to 40% w/w, for example from 5 to 40% w/w;
- fruit in an amount ranging from 0 to 25% w/w, for example from 1 to 18% w/w.

In another aspect, the present invention provides a complementary nutritional composition comprising:
- cereal flour in amount ranging from 20 to 90% w/w, for example to 55% w/w;
- sugar in amount ranging from 0 to 30% w/w, for example from 0 to 20% w/w, for example between 5 to 18% w/w;
- added sugar with low glycemic index in amount ranging from 0 to 30% w/w, for example from 1 to 20% w/w, for example from to 15% w/w;
- fat in an amount ranging from 8 to 20% w/w of the composition, for example ranging from 10 to 17% w/w, for example from 10 to 15% w/w;
- total amount of dietary fiber in amount ranging from 0 to 25% w/w, for example from 2 to 25% w/w;
- added fiber in amount ranging from 0 to 20% w/w;
- milk-based ingredient in an amount ranging from 0 to 30% w/w, for example from 1 to 25% w/w, for example from 5 to 25% w/w;
- legume in amount ranging from 0 to 40%, for example from 1 to 40%, for example from 5 to 40% w/w;
- fruit in an amount ranging from 0 to 25% w/w, for example from 1 to 18% w/w;

for use in treatment, prevention and/or reducing the risk of a metabolic syndrome disorder appearing later in life.

In another aspect, the present invention provides provides a method of treating, preventing, and/or reducing the risk that an infant or young child will develop a metabolic syndrome disorder later in life; in particular when challenged with adipogenic diet, said method comprising the step of administering at an age of the infant or young children comprised between 4 months and 5 year, a nutritional composition comprising:
- cereal flour in amount ranging from 20 to 90% w/w, for example 30 to 55% w/w;
- sugar in amount ranging from 0 to 30% w/w, for example from 0 to 20% w/w, for example between 5 to 18% w/w;
- added sugar with low glycemic index in amount ranging from 0 to 30% w/w, for example from 1 to 20% w/w, for example from 5 to 15% w/w;
- fat in an amount ranging from 8 to 20% w/w of the composition, for example ranging from 10 to 17% w/w, for example from 10 to 15% w/w;
- total amount of dietary fiber in amount ranging from 0 to 25% w/w, for example from 2 to 25% w/w;
- added fiber in amount ranging from 0 to 20% w/w;
- milk-based ingredient in an amount ranging from 0 to 30% w/w, for example from 1 to 25% w/w, for example from 5 to 25% w/w;
- legume in amount ranging from 0 to 40%, for example from 1 to 40% w/w, for example from 5 to 40% w/w;
- fruit in an amount ranging from 0 to 25% w/w, for example from 1 to 18% w/w.

In a further aspect, the present invention provides a complementary nutritional set which comprises a complementary nutritional composition comprising:
- cereal flour in amount ranging from 20 to 90% w/w, for example from 30 to 55% w/w;
- sugar in amount ranging from 0 to 30% w/w, for example from 0 to 20% w/w, for example between 5 to 18% w/w;
- added sugar with low glycemic index in amount ranging from 0 to 30% w/w, for example from 1 to 20% w/w, for example from 5 to 15% w/w;
- fat in an amount ranging from 8 to 20% w/w of the composition, for example ranging from 10 to 17% w/w, for example from 10 to 15% w/w;
- total amount of dietary fiber in amount ranging from 0 to 25% w/w, for example from 2 to 25% w/w;
- added fiber in amount ranging from 0 to 20% w/w;
- milk-based ingredient in an amount ranging from 0 to 30% w/w, for example from 1 to 25% w/w, for example from 5 to 25% w/w;
- legume in amount ranging from 0 to 40%, for example from 1 to 40%, for example from 5 to 40% w/w;
- fruit in an amount ranging from 0 to 25% w/w, for example from 1 to 18% w/w.

BRIEF DESCRIPTION OF THE SEVERAL VIEWS OF THE DRAWING(S)

DEFINITIONS

Figure 1:
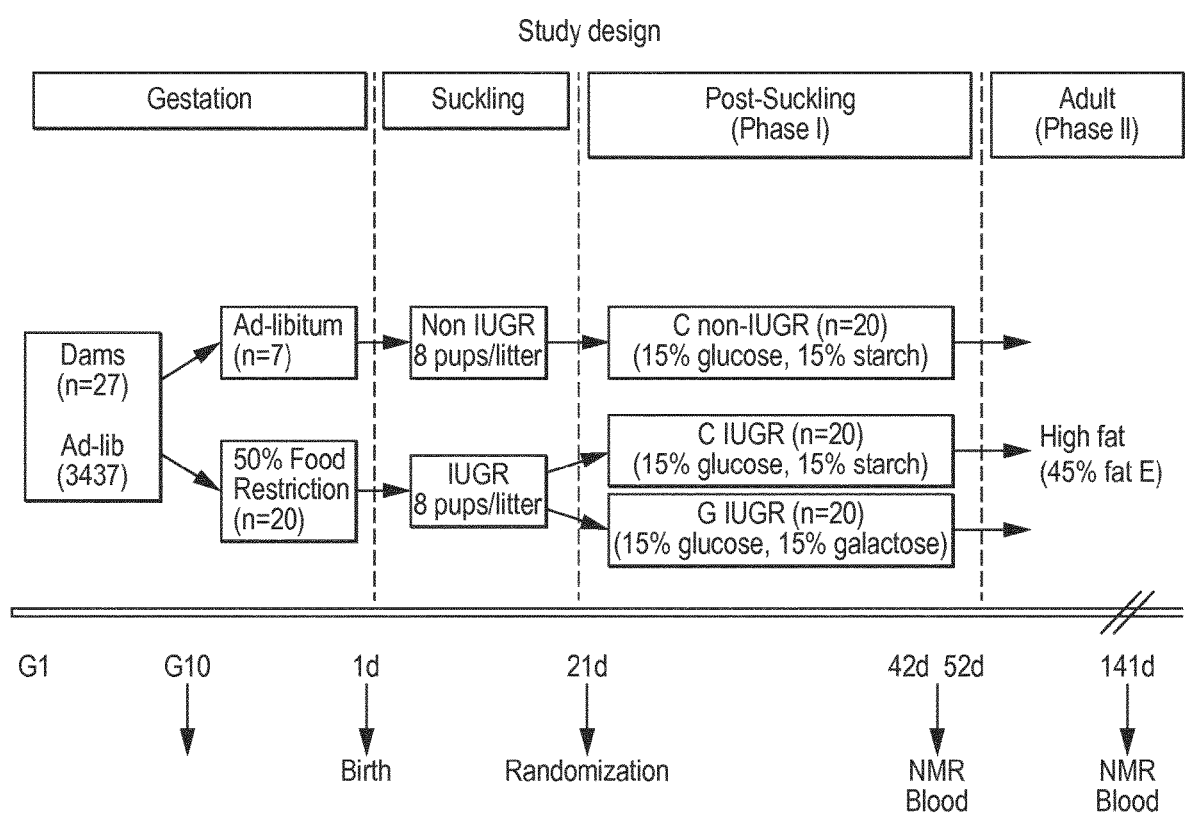
FIG. 1 shows a diagram of the experimental design of the study described in Example 1.

Prior to discussing the present invention in further details, the following terms and conventions will first be defined:

In the context of the present invention, mentioned percentages are weight/weight percentages unless otherwise stated.

The term "and/or" used in the context of the "X and/or Y" should be interpreted as "X", or "Y", or "X and Y".

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 1 to 8, from 3 to 7, from 4 to 9, from 3.6 to 4.6, from 3.5 to 9.9, and so forth.

All references to singular characteristics or limitations of the present invention shall include the corresponding plural characteristic or limitation, and vice versa, unless otherwise specified or clearly implied to the contrary by the context in which the reference is made.

Unless defined otherwise, all technical and scientific terms used herein have the same meaning as commonly understood by one of ordinary skill in the art.

The term "infant" means a child under the age of 12 months.

The term "young child" means a child older than 12 months and up until 5 years of age (including toddlers).

The expression "child" generally indicates a human up to the age of eighteen.

A "preterm" or "premature" means an infant or young child that was not born at term. Generally it refers to an infant born prior to the completion of 37 weeks of gestation.

The expression "Term born infant" indicates an infant born after 37 weeks gestation.

Within the context of the present invention, the term "Low birth weight" indicates a newborn's body weight below 2500 g (5.5 pounds), either as a result of preterm birth (i.e. before 37 weeks of gestation) and/or due to restricted foetal growth.

Within the context of the present invention, the term "Small-for-gestational-age (SGA)" refers to babies with birth weights below the 10th percentile for babies of the same gestational age.

The expression "Postnatal period" is the period beginning immediately after the birth of a child and extending for about six weeks.

The expression "nutritional composition" means a composition which nourishes a subject. This nutritional composition is usually to be taken enterally, orally, parenterally or intravenously, and it usually includes one of more nutrients selected from: a lipid or fat source, a protein source. and a carbohydrate source. Preferably, a nutritional composition is for oral use.

The expression "synthetic composition" means a mixture obtained by chemical and/or biological means, which can be chemically identical to the mixture naturally occurring in mammalian milks. In one embodiment of the present invention, the complementary nutritional composition is a synthetic composition.

The expression "infant formula" means a foodstuff intended for particular nutritional use by infants during the first four to six months of life and satisfying by itself the nutritional requirements of this category of person (Article 1.2 of the European Commission Directive 91/321/EEC of May 14, 1991 on infant formulae and follow-on formulae).

The expression "follow-on formula" means a foodstuff intended for particular nutritional use by infants aged over four months and constituting the principal liquid element in the progressively diversified diet of this category of person.

Within the context of the present invention, the term "Growing up milk (GUM)" indicates nutritional formula which may be given to children from age of 12 months, in some instances after stopping the infant formula. The "growing-up milks" (or GUMs) are given from one year onwards. It is generally a milk-based beverage adapted for the specific nutritional needs of young children.

In the present context the term "infant cereal product" relates to a cereal product that has been designed specifically for infants in order to provide the required nutritional contribution to the infant.

The expression "baby food" means a foodstuff intended for particular nutritional use by infants during the first years of life.

The expression "fortifier" refers to liquid or solid nutritional compositions suitable for mixing with breast milk or infant formula.

The "mother's milk" should be understood as the breast milk or colostrum of the mother (=Human Breast Milk=HBM).

The term "complementary feeding period" indicates the process of gradually introducing a mammal infant to what will be its adult diet and complementing the supply of its mother's milk with solid foods. For humans, the complementary feeding period typically starts at age between 4 and 6 months of infant's age and is considered completed once the infant is not anymore fed with any breast milk (or substitute infant formula), typically at 24 months. In one embodiment, the complementary feeding period is comprised between 4, for example 6, months and 24, for example 18 months of infant's age.

The expression "complementary nutritional composition" or "a nutritional composition for complementary feeding period" means a nutritional composition as above defined which is designed to be administered to an infant or young child at the time the complementary feeding period starts or afterwards. In one embodiment, the complementary nutritional composition is administered during the complementary feeding period. This nutritional composition is usually to be taken enterally, orally, parenterally or intravenously, and it usually includes a lipid or fat source, a protein source and a carbohydrate source. Optionally, this nutritional compositions also comprise vitamins and minerals. Preferably, a nutritional composition is for oral use. Non-limiting examples of complementary nutritional compositions are: infant cereal products, follow-on formula, GUMS, baby food. Infant cereal products may be grouped in two main categories: complete cereal product which need to be reconstituted in water as they already contain all the necessary nutrients to be delivered with the meal; and standard cereal product which are meant to be reconstituted with milk, infant formula, follow-on formula and/or GUMs.

The term "reducing the risk of" means that the event is less likely to happen compared to the appropriate and usual reference (such as a general population or normal weight infants or young children).

The term "prevention" means that the event or disorder is prevented from taking place either completely, or partially (i.e., a milder form occurs and/or occurs later). The terms prevention also comprises a reduction in the severity of the event or disorder (or health condition) or a reduction in the frequency of occurrence of such events or disorders or a delaying effect on such events or disorders.

The terms "normal weight/overweight/underweight" refer to the internationally recognized tables for weight of infants, young children and children, and is in particular function of the age of the subject.

The expression "Glycemic index" or "Glycaemic index" (GI) in the context of the present invention indicates a number associated with a particular type of food/composition and/or ingredient that indicates the food's effect on a person's blood glucose level. A value of 100 represents the standard, an equivalent amount of pure glucose. The GI represents the total rise in a person's blood sugar level following consumption of the food/composition/ingredient. The glycemic index of a food is defined as the incremental area under the two-hour blood glucose response curve (AUC) following a 12-hour fast and ingestion of a food with a certain quantity of available carbohydrate (usually 50 g). The incremental AUC of the test food is divided by the incremental AUC of the standard (either glucose or white bread, giving two different definitions) and multiplied by 100. The average GI value is calculated from data collected in 10 human subjects. Both the standard and test food must contain an equal amount of available carbohydrate. The result gives a relative ranking for each tested food—The current validated methods use glucose as the reference food, giving it a glycemic index value of 100 by definition.

The glycemic index of an ingredient or food composition may be measured according to the method described in ISO (International Organization for Standardization) 26642:2010 (en).

Tables are available in the literature that list many types of foods and their GIs (see for example: "International table of glycemic index and glycemic load values: 2002", Foster-Powell et al., The American Journal of Clinical Nutrition, 2002, 76: 5-56)

In one embodiment, when reference to GI is made in the context of the present invention, it is intended the GI for that particular ingredient or food which has been measured in healthy adults subjects.

Within the context of the present invention, the term "glycemic load" or "glycaemic load" (GL) of food is a number that estimates how much a serving of a food composition will raise a person's blood glucose after eating it. Glycemic load accounts for how much carbohydrate is in a serving of food and how much each gram of carbohydrate in the serving of food raises blood glucose levels. Glycemic load is based on the glycemic index (GI) of ingredients in the food composition, and is calculated by multiplying the grams of available carbohydrate in the food times the available carbohydrate GI and then dividing by 100.

Glycemic Load in a serving of food with different type and amount of available carbohydrate (CHO) is calculated as the sum of (GI of available CHO A per serving×weight of CHO A in food)+(GI of available CHO B x weight of CHO B per serving in food)+the same for each of available CHO in food/100.

The appropriate serving size would be apparent to the person skilled in the art for each type of food.

By way of guidance, exemplary serving size of use in the calculation of GL for infants are below provided:

Complete infant cereal (to be reconstituted in water in 150 mL)=50 g Standard infant cereal (to be reconstituted in 160 mL of infant formula)=25 g Infant Formula=100 mL Baby food=100 g.

Within the context of the present invention, the term "glucose response" (GR) indicates the post prandial blood glucose response (change in blood concentration) elicited when one serving of food is ingested and it is measured upon consumption of a serving of food regardless of the amount of available carbohydrate.

The glucose response may be measured as below described:

Glucose concentration in blood samples (capillary) is analysed using calibrated YSI 2300 Stat Plus Glucose and Lactate analyser.

The increase in the blood glucose concentration at different time point (15 to 120 minutes after intake of test meals) is calculated by reduction of the base-line value (blood glucose before intake of test meals) from each values.

The total increase under two-hour blood glucose response curve (IAUC) is calculated using the trapezoidal rule.

The results may be expressed as the % of response relative to one reference product.

Within the context of the present invention, the term "Insulin index" (II) indicates a number associated with a particular type of food/composition and/or ingredient that indicates the food's effect on a person's blood insulin level. The index is similar to the Glycemic Index (GI), but rather than relying on blood glucose, the II is based upon blood insulin levels.

The II may calculated based on 2 hours increase in plasma insulin concentration upon a consumption of a test food compared to an isoenergetic food (1000 kJ bread) or upon consumption of a test food with 50g available carbohydrate (compared to 50g glucose).

The insulin index of an ingredient or food composition may be measured according to the method described in the paper "An insulin index of food: the insulin demand generated by 100kJ portions of common foods", Holt HA S. et al, The American Journal of Clinical Nutrition, 1997; 66; 1264-76)

Within the context of the present invention, the term "insulin response" (IR) indicates the 2 hours post prandial blood insulin response (change in concentration) elicited with quantity of tested food or meal ingested and it is measured as the plasma insulin curve upon consumption of a test food compared to an adequate reference.

The insulin response may be measured as below described:

The concentration of plasma insulin concentration is measured by Human Insulin Immunoassay Kit.

The increase in the plasma insulin concentration at different time points was calculated as is explain above for glucose (under GR);

The % response relative to reference product may be calculated as explained above for glucose.

The expression "nutritional composition characterized by low Glycaemic index" in the context of the present invention indicates a nutritional composition having a glycemic index equal or lower than 70. For example, the glycemic index of such nutritional composition may be in one embodiment lower or equal to 65, lower or equal to 60, lower or equal to 55, lower or equal to 50. The expression has to be intended as opposed to "nutritional composition characterized by high Glycaemic index" which indicates a nutritional composition having a glycemic index higher than 70.

The expression "ingredient with low glycemic index" in the context of the present invention indicates a food ingredient having a glycemic index equal or lower than 70. For example, the glycemic index of such carbohydrate-based ingredient may be in one embodiment lower or equal to 65, lower or equal to 60, lower or equal to 55, lower or equal to 50, lower or equal to 45.

In the context of the present invention, the expression "nutritional composition characterized by low Glycaemic load" or "low glycaemic load nutritional composition" indicates a nutritional composition having a glycemic load equal or lower than 20. The expression has to be intended as opposed to "nutritional composition characterized by high Glycaemic load" which indicates a nutritional composition having a glycemic load higher than 20. For example, the glycemic load of such low glycaemic load nutritional composition may be in one embodiment lower or equal to 19, lower or equal to 17, lower or equal to 15. In one embodiment, the glycaemic load has a value ranging from 15 to 20, for example from 16 to 19.

The expression "carbohydrate-based ingredient" or "carbohydrate-based ingredients" in the context of the present invention indicates a food ingredient consisting of or comprising one or more carbohydrates. Non limiting examples of carbohydrate based ingredients are: cereal flours (for example whole grain or refined flour from maize, wheat, rice, oat), cereal starches (for example from maize, wheat, oath, rice) sugars [honey, monosaccharides (eg. Galactose, fructose, glucose), disaccharides (eg. Sucrose, lactose, isomaltulose, maltose)], oligosaccharides (fructo-oligosaccharides, galacto-oligosaccharides, gluco-oligosaccharides, maltodextrines),polysaccharides (eg. resistant starches), fibers (soluble and insoluble), pulses [for example Green lentils, red lentils, yellow lentils, mung bean, cow peas, chick peas, butter bean, black eye bean, kidney bean, pea, pigeon pea, soya bean, haricot & navy beans, blacked bean, Soybean, Pea, Lupin, Faba bean, Mung Beans, Chickpeas, Cowpea, Lentils (red, yellow, green), Carob, Beans white/green/black/red, Navy beans, Lima beans, Pinto beans, Pigeon Pea, Black gram, Carioguinha beans, Bambara bean (Vigna subterranean), Yam bean, Canola flour, Flaxseed Powder, Chestnut flour], fruit, milk-based ingredients (for example powder skimmed or whole milk).

The expressions "sugar" or "sugars" within the context of the present invention comprises available monosaccharides (eg. Galactose, fructose, glucose) available disaccharides (eg. Sucrose, lactose, isomaltulose, maltose) or mixtures thereof.

Within the context of the present invention the term "added sugar" indicates an ingredient mainly or totally constituted by sugar which is added to the complementary nutritional composition and whose content in sugar contributes to the total sugar content of the composition.

The total sugar content of the complementary nutritional composition is provided by the sum of amount of sugar naturally present in ingredients used in the recipe (for example from cereal flour), those possibly produced during processing plus amount of added sugar. As it will be apparent to the person skilled in the art, the total amount of sugars will also comprise any sugar amount which may be released by ingredients used in the recipe during processing due to the specific conditions used (for example comprising partial hydrolysis of starch). Determination of total sugars in the complementary nutritional composition according to the invention may be carried out according to methods well known to the person skilled in the art.

For example, for quantification of total sugars in Infant cereals products the following method can be used:

The quantification of mono- and disaccharides in infant cereal samples can be completed by weighing a 1-3±0.001 gram sample into a 100 mL volumetric flask and 60 milliliters of demineralized water were added. Mono- and disaccharides contained in the samples are extracted by placing the flasks into a 70° C. water bath for 20 min with constant agitation. Samples are cooled to room temperature and more demineralized water is added to make up the mark on each volumetric flask, stoppers placed and closed flasks were shaken vigorously. Samples are then filtered through folded filter paper (N° 597, 150 mm ∅) and through a 0.2 μm HPLC-filter before injection (25 mm ∅, 8825-P-2 Infochroma AG). A solution containing monomeric glucose, dimeric lactose, sucrose, maltose, isomaltulose, and maltooligosaccharides having a degree of polymerization ranging from 3-7 is prepared as standard for peak identification and saccharide quantification.

Filtered samples are injected into chromatograph after degassing the eluents (demineralized water, 18 MΩ·cm minimum; 300 mM NaOH; 500 mM NaOH with 150 mM NaOAc) by sparging helium for 20-30 min and allowing the system to equilibrate. The following chromatographic conditions may be used: CarboPac PA1 (Dionex) column and guard column; 20 μL injection volume; 300 mM NaOH eluent with 0.6 mL/min flow rate as post column addition; 22° C. temperature.

The expression "milk-based ingredient" or "milk-based ingredients" in the context of the present invention identifies carbohydrate containing ingredients derived from mammal milk for example cow, goat and/or buffalo or mixtures thereof. Non limiting examples of such ingredients comprise: fresh milk, concentrated milk, powder milk, whole milk, skimmed and/or semi-skimmed milk.

As it will be apparent to the skilled person, milk-based ingredients according to the present invention may bring additional nutrients beyond carbohydrates to the complementary nutritional composition, such as for example proteins and fats.

Within the context of the present invention the term "added sugar with low glycemic index" indicates added sugar as above defined which is caractherized by having a low glycaemic index. For the sake of clarity, the amount of lactose contained in any milk-based ingredient used in the recipe, will also account as added sugar with low glycaemic index.

The expressions "fiber" or "fibers" or "dietary fiber" or "dietary fibers" within the context of the present invention indicate the indigestible portion, in small intestine, of food derived from plants which comprises two main components: Soluble fiber, which dissolves in water and insoluble fiber. Mixtures of fibers are comprised within the scope of the terms above mentioned. Soluble fiber is readily fermented in the colon into gases and physiologically active byproducts, and can be prebiotic and viscous. Insoluble fiber does not dissolve in water, is metabolically inert and provides bulking, or it can be prebiotic and metabolically ferment in the large intestine. Chemically, dietary fiber consists of non-starch polysaccharides such as arabinoxylans, cellulose, and many other plant components such as resistant starch, resistant dextrins, inulin, lignin, chitins, pectins, beta-glucans, and oligosaccharides. Non limiting examples of dietary fibers are: prebiotic fibers such as Fructo-oligosaccharides (FOS), inulin, galacto-oligosaccharides (GOS), fruit fiber, vegetable fiber, cereal fiber, resistant starch such as high amylose corn starch. As fibers are not digestible, they do not contain available carbohydrates and on this basis they do not contribute to the GI or GL of the composition they're part of.

Within the context of the present invention the term "added fiber" or "added dietary fiber" indicates an ingredient mainly or totally constituted by fiber which is added to the complementary nutritional composition and whose content in fiber contributes to the total fiber content of the composition. The total fiber content of the complementary nutritional composition is provided by the sum of amount of fiber naturally present in ingredients used in the recipe (for example from whole grain cereal flour) plus amount of added fiber.

Within the context of the present invention, the term "legume" or "legumes" identifies the fruit or seed of a plant in the family of Fabaceae or mixtures thereof. Well-known legumes include inter alia alfalfa, clover, peas, beans, lentils, lupins, mesquite, carob, soybeans, peanuts and tamarind. The grain seeds of such plants are generally known as "pulses" and are comprised within the scope of the term "legumes" according to the present invention.

As it will be apparent to the skilled person, legumes according to the present invention may bring additional nutrients beyond carbohydrates to the complementary nutritional composition, such as for example vitamins, minerals, proteins of vegetable origin and/or fibers.

Within the context of the present invention, the term "fruit" or "fruits" indicates ingredients derived from fruit such as for example fresh fruit, fruit paste, dried fruit, fruit extracts and/or centrifugates. Mixtures of such ingredients are also comprised within the scope of the terms above mentioned. Non limiting examples of fruit according to the present invention are: apple, apricot, banana, cherry, pear, strawberry, Mango, Orange, peach.

The expression "carbohydrate-based ingredient with low glycemic index" in the context of the present invention indicates a carbohydrate-based ingredient having a glycemic index equal or lower than 70. For example, the glycemic index of such carbohydrate-based ingredient may be in one embodiment lower or equal to 65, lore or equal to 60, lower or equal to 55, lower or equal to 50, lower or equal to 45.

Non limiting examples of carbohydrate based ingredients with low glycemic index may be: cereal flours (for example whole grain or refined flour from maize, wheat, rice, oat), sugars [monosaccharides (eg. Galactose, fructose), disaccharides (eg. Sucrose, lactose, isomaltulose), oligosaccharides (fructo-oligosaccharides, galacto-oligosaccharides, gluco-oligosaccharides)], polysaccharides (eg. resistant starches), fibers (soluble and insoluble), legumes [especially pulses for example Green lentils, red lentils, yellow lentils, mung bean, cow peas, chick peas, butter bean, black eye bean, kidney bean, pea, pigeon pea, soya bean, haricot & navy beans, blacked bean, Soybean, Pea, Lupin, Faba bean, Mung Beans, Chickpeas, Cowpea, Lentils (red, yellow, green), Carob, Beans white/green/black/red, Navy beans, Lima beans, Pinto beans, Pigeon Pea, Black gram, Potato protein isolate, Carioguinha beans, Bambara bean (Vigna subterranean), Yam bean, Canola flour, Sunflower protein, Hemp, Flaxseed Powder, Chestnut flour], fruit (for example dried fruit or fruit paste), milk-based ingredients, such as powder skimmed or whole milk.

The glycemic index of low glycemic index sugars is in one embodiment of the present invention lower or equal to 70, lower or equal to 60, lower or equal to 45, lower or equal to 35, lower or equal to 30. In one embodiment, the GI of low glycemic index sugars is ranging from 0 to 55, for example from 0 to 40. In one embodiment, sugar is selected for example from the group consisting of: Galactose, fructose, Sucrose, lactose and isomaltulose.

The glycemic index of legumes is in one embodiment of the present invention lower or equal to 55, lower or equal to 50, lower or equal to 45, lower or equal to 35, lower or equal to 30. In one embodiment, the GI of legumes is ranging from 15 to 40, for example from 20 to 35.

The glycemic index of milk-based ingredients is in one embodiment of the present invention lower or equal to 55, lower or equal to 50, lower or equal to 45, lower or equal to 35. In one embodiment, the GI of milk-based ingredients is ranging from 20 to 40, for example from 25 to 35.

The glycemic index of fruit is in one embodiment of the present invention lower or equal to 55, lower or equal to 50, lower or equal to 45, lower or equal to 35, lower or equal to 30. In one embodiment, the GI of legumes is ranging from 15 to 40, for example from 20 to 35. In one embodiment, fruit is dried fruit selected for example from the group consisting of: apple, apricot, banana, cherry, pear, strawberry, Mango, Orange and peach.

The expression "fat" or "fat source" or "lipid" or "lipid source" or "fats" in the context of the present invention indicates an edible solid or liquid fat or mixtures thereof. Not limiting categories of fats are those from animal, fish or vegetable origins. Non limiting examples of fats which could be used according to the present invention are: fish oil, cocoa butter, cocoa butter equivalents (CBE), cocoa butter substitutes (CBS), vegetable oils (for example rapeseed oil, palm oil, corn oil, soy oil, coconut oil and/or sunflower oil) and butter oils amongst others.

Within the context of the present invention, the term "complementary nutritional set" indicates all the food, either in liquid or solid form, which is ingested by an infant or young child on a daily basis during the complementary feeding period. According to the present invention, the complementary nutritional set comprises a complementary nutritional composition characterized by and/or comprising an ingredient with a low glycaemic index. In one embodiment, the complementary nutritional composition according to the present invention provides at least 10%, for example 20%, or 30%, or 50%, or 70% or 90% of the total caloric content of the complementary nutritional set wherein it is comprised.

In the context of the present invention, where amounts of certain ingredients (such as, for example, sugars, fats, dietary fibers etc), are indicated which may result from different constituents incorporated in the recipe then such amounts will reflect the total content of that ingredient in the composition, irrespective of the component it is derived from.

On the other hand, when in the present invention reference is made to an "added" ingredient (such as for example added fibers, added sugars with low glycemic index etc), then only the amount of the component mainly or totally constituted by that ingredient should be accounted in the calculation.

Composition for Use

The invention in a first aspect relates to a complementary nutritional composition characterized by a low glycemic load for use in treatment, prevention and/or reducing the risk of a metabolic syndrome disorder appearing later in life.

The invention also relates to a complementary nutritional composition characterized by a low glycemic index for use in treatment, prevention and/or reducing the risk of a metabolic syndrome disorder appearing later in life.

The invention also relates to a complementary nutritional composition characterized by a low glycemic load and index for use in treatment, prevention and/or reducing the risk of a metabolic syndrome disorder appearing later in life.

In one embodiment of the present invention, the complementary nutritional composition is characterized by eliciting a low glucose response in the subject assuming it.

In one embodiment of the present invention, the complementary nutritional composition is characterized by eliciting a low insulin response in the subject assuming it.

In one embodiment of the present invention, the complementary nutritional composition is characterized by eliciting a low glucose and insulin response in the subject assuming it.

In one embodiment of the present invention, complementary nutritional composition characterized by a low glycaemic index is achieved by reducing the quantity of a carbohydrate-based ingredient by any mean.

In another aspect, the complementary nutritional composition of the present invention comprises at least one ingredient with low glycemic index.

In one embodiment, the complementary nutritional composition according to the present invention comprises one cereal flour or mixtures thereof. In one embodiment, the cereal flour may be refined or whole grain. In a further embodiment, the cereal flour may be refined or whole grain maize, wheat, rice, oat, corn or barley flour.

In one embodiment, the complementary nutritional composition of the present invention comprises an amount of cereal flours ranging from 20 to 90% w/w, for example 20 to 70% w/w.

In one embodiment, when the complementary nutritional composition is an infant cereal product, for example a complete infant cereal product, it comprises an amount ranging from 30 to 55% w/w of cereal flours. In one embodiment, it comprises 0 to 30% w/w of refined flour and 0 to 55% of whole grain flours.

In one embodiment, when the complementary nutritional composition is an infant cereal product, for example a standard infant cereal product, it comprises an amount ranging from 40 to 85% w/w or 50 to 90% w/w of cereal flours. In one embodiment, it comprises 30 to 50% w/w of refined flour and 20 to 40% of whole grain flours.

In one embodiment, the complementary nutritional composition of the present invention comprises at least one carbohydrate-based ingredient with low glycemic index.

In a further embodiment, the complementary nutritional composition of the present invention comprises at least one carbohydrate-based ingredient selected from the group consisting of: Resistant starches, Amylose, Sucrose, Lactose, Isomaltulose, Maltitol, Galactose, Fructose, Isomalt, Xilitol and Polydextrose.

In one embodiment, the complementary nutritional composition of the present invention comprises a sugar or mixtures thereof.

In one embodiment, the total amount of sugars in the complementary nutritional composition according to the invention ranges from 0 to 30% w/w, preferably from 0 to 20, for example between 5 to 18% w/w.

In one embodiment, for example when the product is an infant cereal complete product, the total amount of sugars in the complementary nutritional composition according to the invention ranges from 0 to 30% w/w, preferably from 2 to 25, for example between 5 to 25% w/w.

In one embodiment, for example when the product is an infant cereal standard product, the total amount of sugars in the complementary nutritional composition according to the invention ranges from 0 to 30% w/w, preferably from 2 to 25, for example between 5 to 20% w/w.

In another embodiment, the amount of added sugars in the complementary nutritional composition ranges from 0 to 30% w/w, for example from 1 to 20% w/w or from 5 to 15% w/w.

In one embodiment, the complementary nutritional composition of the present invention comprises an amount of added sugars with low glycemic index which ranges from 0 to 30% w/w, for example from 1 to 20% w/w or from 5 to 15% w/w. For example the low glycemic index sugar may be selected in the group consisting of: lactose, galactose, fructose, and isomaltulose.

In one embodiment, the complementary nutritional composition of the invention comprises an edible fat or mixtures thereof, for example it comprises vegetable oils (for example rapeseed oil, palm oil, corn oil, soy oil, coconut oil and/or sunflower oil) and/or fats derived from milk. In a further embodiment, the complementary nutritional composition comprises fats in an amount ranging from 8 to 20% w/w of the composition, for example ranging from 10 to 20% w/w, for example ranging from 10 to 17% w/w or from 10 to 15% w/w.

In one embodiment, the energy provided by fats in the composition ranges from 22 to 40%, for example between 27 and 38% of the total energy intake provided by the complementary composition according to the invention.

In one embodiment, the complementary nutritional composition according to the present invention doesn't comprise fats. In such embodiment, the complementary nutritional composition of the invention may be a standard cereal product as above defined.

In one embodiment, the complementary nutritional composition according to the invention comprises a dietary fiber or mixtures thereof. In one embodiment, the total amount of dietary fibers in the complementary nutritional composition according to the invention ranges from 0 to 25% w/w, for example from 2 to 22% w/w; for example from 2 to 12% w/w, for example from 6 to 10% w/w.

In another embodiment, when the complementary nutritional composition is a complete infant cereal product, the amount of added fibers in the complementary nutritional composition ranges from 0 to 10% w/w, for example from 1 to 8% w/w or from 1.5 to 7% w/w.

In a further embodiment, when the complementary nutritional composition is a standard infant cereal product, the amount of added fibers in the complementary nutritional composition ranges from 0 to 20% w/w, for example from 5 to 18% w/w.

In one embodiment, the complementary nutritional composition according to the present invention comprises a milk-based ingredient or mixtures thereof. In one embodiment, the complementary nutritional composition comprises a milk-based ingredient in an amount ranging from 0 to 35% w/w, for example 0 to 30% w/w, for example from 1 to 25% w/w, for example from 5 to 25% w/w.

In a further embodiment, the complementary nutritional composition comprises milk-based ingredients having a GI lower or equal to 30 in an amount ranging from 0 to 35% w/w, for example 0 to 30% w/w, for example from 1 to 25% w/w, for example from 5 to 25% w/w.

In one embodiment, the complementary nutritional composition according to the present invention comprises a legume or mixtures thereof.

In one embodiment, the complementary nutritional composition comprises legumes in an amount ranging from 5 to 40% w/w, for example from 8 to 30% w/w, for example from 10 to 25% w/w.

In a further embodiment, the complementary nutritional composition comprises legumes having a GI lower or equal to 50 in an amount ranging from 5 to 40% w/w, for example from 8 to 30% w/w, for example from 10 to 25% w/w.

In one embodiment, the complementary nutritional composition according to the present invention comprises a fruit or mixtures thereof.

In one embodiment, the complementary nutritional composition comprises fruits in an amount ranging from 0 to 25% w/w, for example from 1 to 18% w/w.

In a further embodiment, the complementary nutritional composition comprises fruits having a GI lower or equal to 70, for example lower or equal to 50 in an amount ranging from 0 to 20% w/w, for example from 1 to 15% w/w.

In one embodiment, the present invention provides a complementary nutritional composition comprising:
  cereal flour in amount ranging from 20 to 90% w/w;
  sugar in amount ranging from 0 to 30% w/w, for example from 0 to 20% w/w, for example between 5 to 18% w/w;
  added sugar with low glycemic index in amount ranging from 0 to 30% w/w, for example from 1 to 20% w/w, for example from 5 to 15% w/w;
  fat in an amount ranging from 8 to 20% w/w of the composition, for example ranging from 10 to 17% w/w, for example from 10 to 15% w/w;
  total amount of dietary fiber in amount ranging from 0 to 25% w/w, for example from 2 to 25% w/w;
  added fiber in amount ranging from 0 to 20% w/w;
  milk-based ingredient in an amount ranging from 0 to 30% w/w, for example from 1 to 25% w/w, for example from 5 to 25% w/w;
  legume in amount ranging from 0 to 40%, for example from 5 to 40% w/w;
  fruit in an amount ranging from 0 to 25% w/w, for example from 1 to 18% w/w.

In one embodiment, the above described complementary nutritional composition is characterized by a low glycemic index and/or a low glycemic load. In one embodiment, the above described complementary nutritional composition of the invention is an infant cereal product. In one embodiment, the above described complementary nutritional composition is characterized by eliciting a low glucose and/or insulin response in the subject assuming it. In one embodiment, the above described complementary nutritional composition of the invention is for use in treatment, prevention and/or reducing the risk of a metabolic syndrome disorder appearing later in life.

In one embodiment, the present invention provides a complementary nutritional composition comprising:
  cereal flour in amount ranging from 20 to 70% w/w, for example 30 to 55% w/w of cereal flours;
  sugar in amount ranging from 0 to 30% w/w, for example from 0 to 20% w/w, for example between 5 to 18% w/w;
  added sugar with low glycemic index in amount ranging from 0 to 30% w/w, for example from 1 to 20% w/w, for example from 5 to 15% w/w;
  fat in an amount ranging from 8 to 20% w/w of the composition, for example ranging from 10 to 17% w/w, for example from 10 to 15% w/w;
  total amount of dietary fiber in amount ranging from 2 to 12% w/w, for example from 6 to 10% w/w;
  added fiber in amount ranging from 0 to 10% w/w, for example from 1 to 8% w/w, for example from 1.5 to 7% w/w;
  milk-based ingredient in an amount ranging from 0 to 35% w/w, for example 0 to 30% w/w, for example from 1 to 25% w/w, for example from 5 to 25% w/w;
  legume in amount ranging from 5 to 40% w/w, for example from 8 to 30% w/w, for example from 10 to 25% w/w;
  fruit in an amount ranging from 0 to 25% w/w, for example from 1 to 18% w/w.

In another embodiment, the present invention provides a complementary nutritional composition comprising:
  cereal flour in amount ranging from 20 to 70% w/w, for example 30 to 55% w/w of cereal flours, for example 33 to 50% w/w;
  sugar in amount ranging from 0 to 30% w/w, for example from 0 to 25% w/w, for example from 5 to 25% w/w, for example from 0 to 20% w/w, for example between 5 to 18% w/w;
  added sugar with low glycemic index in amount ranging from 0 to 30% w/w, for example from 1 to 20% w/w, for example from 5 to 15% w/w;
  fat in an amount ranging from 8 to 20% w/w of the composition, for example ranging from 10 to 17% w/w, for example from 10 to 15% w/w;
  total amount of dietary fiber in amount ranging from 2 to 12% w/w, for example from 6 to 10% w/w;
  added fiber in amount ranging from 0 to 10% w/w, for example from 1 to 8% w/w, for example from 1.5 to 7% w/w;
  milk-based ingredient in an amount ranging from 0 to 35% w/w, for example from 0 to 30% w/w, for example from 1 to 25% w/w, for example from 5 to 25% w/w;
  legume in amount ranging from 5 to 40% w/w, for example from 5 to 40% w/w, for example from 8 to 30% w/w, for example from 10 to 25% w/w;
  fruit in an amount ranging from 0 to 25% w/w, for example from 1 to 18% w/w.

In an additional embodiment, the present invention provides a complementary nutritional composition comprising:
  cereal flour in amount ranging from 33 to 50% w/w;
  sugar in amount ranging from from 5 to 25% w/w;
  added sugar with low glycemic index in amount ranging from 5 to 15% w/w;
  fat in an amount ranging from 10 to 17% w/w;
  total amount of dietary fiber in amount ranging 6 to 10% w/w;
  added fiber in amount ranging from 0 to 10% w/w, for example from 1 to 8% w/w, for example from 1.5 to 7% w/w;
  milk-based ingredient in an amount ranging from 5 to 25% w/w;
  legume in amount ranging from 5 to 40% w/w, for example from 5 to 40% w/w, for example from 8 to 30% w/w, for example from 10 to 25% w/w;
  fruit in an amount ranging from 0 to 25% w/w, for example from 1 to 18% w/w.

In a further embodiment, the present invention provides complementary nutritional composition comprising:
  cereal flour in amount ranging from 33 to 50% w/w;
  sugar in amount ranging from 5 to 25% w/w;

added sugar with low glycemic index in amount ranging from 5 to 15% w/w;
fat in an amount ranging from 10 to 17% w/w;
total amount of dietary fiber in amount ranging from 6 to 10% w/w;
added fiber in amount ranging from 1.5 to 7% w/w;
milk-based ingredient in an amount ranging from 5 to 25% w/w;
legume in amount ranging from 10 to 25% w/w;
fruit in an amount ranging from 1 to 18% w/w;
wherein the complementary nutritional composition comprises 0 to 30% w/w of cereal refined flour and 0 to 55% of cereal whole grain flours.

In a further embodiment, the present invention provides complementary nutritional composition comprising:
cereal flour in amount ranging from 33 to 50% w/w;
sugar in amount ranging from 5 to 25% w/w;
added sugar with low glycemic index in amount ranging from 5 to 15% w/w;
fat in an amount ranging from 10 to 17% w/w;
total amount of dietary fiber in amount ranging from 6 to 10% w/w;
added fiber in amount ranging from 0 to 10% w/w, for example from 1 to 8% w/w, for example from 1.5 to 7% w/w;
milk-based ingredient in an amount ranging from 5 to 25% w/w;
legume in amount ranging from 10 to 25% w/w;
fruit in an amount ranging from 1 to 18% w/w;
wherein the complementary nutritional composition comprises 0 to 30% w/w of cereal refined flour and 0 to 55% of cereal whole grain flours.

In a further embodiment, the present invention provides complementary nutritional composition comprising:
cereal flour in amount ranging from 33 to 50% w/w;
sugar in amount ranging from 5 to 25% w/w;
added sugar with low glycemic index in amount ranging from 5 to 15% w/w;
fat in an amount ranging from 10 to 17% w/w;
total amount of dietary fiber in amount ranging from 6 to 10% w/w;
added fiber in amount ranging from 1.5 to 7% w/w;
milk-based ingredient in an amount ranging from 5 to 25% w/w;
legume in amount ranging from 10 to 25% w/w;
fruit in an amount ranging from 0 to 25% w/w, for example from 1 to 18% w/w.
wherein the complementary nutritional composition comprises 0 to 30% w/w of cereal refined flour and 0 to 55% of cereal whole grain flours.

In a further embodiment, the present invention provides complementary nutritional composition comprising:
cereal flour in amount ranging from 33 to 50% w/w;
sugar in amount ranging from 5 to 25% w/w;
added sugar with low glycemic index in amount ranging from 5 to 15% w/w;
fat in an amount ranging from 10 to 17% w/w;
total amount of dietary fiber in amount ranging from 6 to 10% w/w;
added fiber in amount ranging from 1.5 to 7% w/w;
milk-based ingredient in an amount ranging from 5 to 25% w/w;
legume in amount ranging from 5 to 40% w/w, for example from 5 to 40% w/w, for example from 8 to 30% w/w, for example from 10 to 25% w/w;
fruit in an amount ranging from 1 to 18% w/w;
wherein the complementary nutritional composition comprises 0 to 30% w/w of cereal refined flour and 0 to 55% of cereal whole grain flours.

In one embodiment, the above described seven complementary nutritional compositions are characterized by a low glycemic index and/or a low glycemic load. In one embodiment, the above described complementary nutritional composition of the invention is a complete infant cereal product. In one embodiment, the above described complementary nutritional composition is characterized by eliciting a low glucose and/or insulin response in the subject assuming it. In one embodiment, the above described complementary nutritional composition of the invention is for use in treatment, prevention and/or reducing the risk of a metabolic syndrome disorder appearing later in life.

In another embodiment, the present invention provides a complementary nutritional composition comprising:
cereal flour in amount ranging from 20 to 90% w/w, for example 40 to 85% w/w of cereal flours;
total sugar in amount ranging from 0 to 30% w/w, for example from 0 to 20% w/w, for example between 5 to 18% w/w;
added sugar with low glycemic index in amount ranging from 0 to 30% w/w, for example from 1 to 20% w/w, for example from 5 to 15% w/w;
fat in an amount ranging from 0 to 10% w/w of the composition, for example ranging from 0 to 8% w/w, for example from 0 to 5% w/w;
total amount of dietary fiber in amount ranging from 0 to 25% w/w, for example from 2 to 22% w/w;
added fiber in amount ranging from 0 to 20% w/w, for example from 5 to 18% w/w;
legume in amount ranging from 5 to 40% w/w, for example from 8 to 30% w/w, for example from 10 to 25% w/w;
fruit in an amount ranging from 0 to 25% w/w, for example from 1 to 18% w/w.

In another embodiment, the present invention provides complementary nutritional composition comprising:
cereal flour in amount ranging from 20 to 90% w/w, for example 40 to 85% w/w, for example for example 50 to 90% w/w of cereal flours;
total sugar in amount ranging from 0 to 30% w/w, for example from 5 to 25% w/w, for example from 0 to 20% w/w, for example from 2 to 20% w/w, for example between 5 to 18% w/w;
added sugar with low glycemic index in amount ranging from 0 to 30% w/w, for example from 1 to 20% w/w, for example from 5 to 15% w/w;
fat in an amount ranging from 0 to 10% w/w of the composition, for example ranging from 0 to 5% w/w,;
total amount of dietary fiber in amount ranging from 0 to 25% w/w, for example from 2 to 22% w/w;
added fiber in amount ranging from 0 to 20% w/w, for example from 5 to 18% w/w;
legume in amount ranging from 5 to 40% w/w, for example from 8 to 30% w/w, for example from 10 to 25% w/w;
fruit in an amount ranging from 0 to 25% w/w, for example from 1 to 18% w/w.

In a further embodiment, the present invention provides complementary nutritional composition comprising:
cereal flour in amount ranging from 50 to 90% w/w;
total sugar in amount ranging from 5 to 18% w/w;
added sugar with low glycemic index in amount ranging from 5 to 15% w/w;

fat in an amount ranging from 0 to 10% w/w of the composition, for example ranging from 0 to 5% w/w,;
total amount of dietary fiber in amount ranging from 2 to 22% w/w;
added fiber in amount ranging from 0 to 20% w/w, for example from 5 to 18% w/w;
legume in amount ranging from 5 to 40% w/w, for example from 8 to 30% w/w, for example from 10 to 25% w/w;
fruit in an amount ranging from 0 to 25% w/w, for example from 1 to 18% w/w.

wherein the complementary nutritional composition comprises 30 to 50% w/w of cereal refined flour and 20 to 40% of cereal whole grain flours.

In a further embodiment, the present invention provides complementary nutritional composition comprising:
cereal flour in amount ranging from 50 to 90% w/w;
total sugar in amount ranging from 5 to 18% w/w;
added sugar with low glycemic index in amount ranging from 5 to 15% w/w;
fat in an amount ranging from 0 to 10% w/w of the composition, for example ranging from 0 to 5% w/w,;
total amount of dietary fiber in amount ranging from 2 to 22% w/w;
added fiber in amount ranging from 5 to 18% w/w;
legume in amount ranging from 10 to 25% w/w;
fruit in an amount ranging from 1 to 18% w/w;
wherein the complementary nutritional composition comprises 30 to 50% w/w of cereal refined flour and 20 to 40% of cereal whole grain flours.

In one embodiment, the above described three complementary nutritional compositions are characterized by a low glycemic index and/or a low glycemic load. In one embodiment, the above described complementary nutritional composition of the invention is a standard infant cereal product. In one embodiment, the above described complementary nutritional composition is characterized by eliciting a low glucose and/or insulin response in the subject assuming it. In one embodiment, the above described complementary nutritional composition of the invention is for use in treatment, prevention and/or reducing the risk of a metabolic syndrome disorder appearing later in life.

In a further embodiment, the present invention provides a complementary nutritional set which comprises a complementary nutritional composition comprising:
cereal flour in amount ranging from 20 to 70% w/w, for example 30 to 55% w/w of cereal flours, for example 33 to 50% w/w;
sugar in amount ranging from 0 to 30% w/w, for example from 0 to 25% w/w, for example from 5 to 25% w/w, for example from 0 to 20% w/w, for example between 5 to 18% w/w;
added sugar with low glycemic index in amount ranging from 0 to 30% w/w, for example from 1 to 20% w/w, for example from 5 to 15% w/w;
fat in an amount ranging from 8 to 20% w/w of the composition, for example ranging from 10 to 17% w/w, for example from 10 to 15% w/w;
total amount of dietary fiber in amount ranging from 2 to 12% w/w, for example from 6 to 10% w/w;
added fiber in amount ranging from 0 to 10% w/w, for example from 1 to 8% w/w, for example from 1.5 to 7% w/w;
milk-based ingredient in an amount ranging from 0 to 35% w/w, for example from 0 to 30% w/w, for example from 1 to 25% w/w, for example from 5 to 25% w/w;
legume in amount ranging from 5 to 40% w/w, for example from 5 to 40% w/w, for example from 8 to 30% w/w, for example from 10 to 25% w/w;
fruit in an amount ranging from 0 to 25% w/w, for example from 1 to 18% w/w;
OR
cereal flour in amount ranging from 20 to 90% w/w, for example 40 to 85% w/w, for example for example 50 to 90% w/w of cereal flours;
total sugar in amount ranging from 0 to 30% w/w, for example from 5 to 25% w/w, for example from 0 to 20% w/w, for example from 2 to 20% w/w, for example between 5 to 18% w/w;
added sugar with low glycemic index in amount ranging from 0 to 30% w/w, for example from 1 to 20% w/w, for example from 5 to 15% w/w;
fat in an amount ranging from 0 to 10% w/w of the composition, for example ranging from 0 to 8% w/w, for example from 0 to 5% w/w;
total amount of dietary fiber in amount ranging from 0 to 25% w/w, for example from 2 to 22% w/w;
added fiber in amount ranging from 0 to 20% w/w, for example from 5 to 18% w/w;
legume in amount ranging from 5 to 40% w/w, for example from 8 to 30% w/w, for example from 10 to 25% w/w;
fruit in an amount ranging from 0 to 25% w/w, for example from 1 to 18% w/w;
OR
Any of the above described complementary composition according to the present invention.

Composition for Use-Disorders

The invention relates to a complementary nutritional composition according to the present invention for use in treatment, prevention and/or reducing the risk of a metabolic syndrome disorder later in life.

In one embodiment, the invention relates to a complementary nutritional composition according to the present invention for use in prevention and/or reducing the risk of a metabolic syndrome disorder later in life.

The term "metabolic syndrome disorder" as used herein refers to one or more disorders associated with Metabolic Syndrome. Examples of such disorders include diabetes such as diabetes mellitus, impaired glucose tolerance, impaired fasting glucose, insulin resistance, hypertension, dyslipidemia, overweight, obesity (particularly central obesity) and microalbuminuria. These disorders are typically a result of a dysregulation of the glucose homeostasis. For example, the disorder can be selected in the group consisting of: diabetes mellitus, impaired glucose tolerance, impaired fasting glucose, insulin resistance, hypertension, overweight and obesity (particularly central obesity).

Thus the invention relates in one embodiment to the composition for use according to the invention wherein the disorder is selected from the group consisting of diabetes mellitus, impaired glucose tolerance, impaired fasting glucose, insulin resistance, hypertension, dyslipidemia, overweight, obesity (particularly central obesity) and microalbuminuria.

In other embodiments, the invention relates to the composition for use according to the invention, wherein the use is to improve insulin sensitivity, to promote normal weight and/or to prevent overweight later in life.

The term "later in life" in the context of the present invention refers to the period of time after childhood, that is after 12 years of age. In embodiments of the invention, the metabolic syndrome disorder appears after 12 years of age, or for example after 15 years of age, such as after 18 years of age, such as after 25 years of age, after 30 years of age, after 35 years of age.

Accordingly, a further embodiment of the invention relates to a composition for use according to the invention wherein the use is in treatment, prevention and/or reducing the risk of a metabolic syndrome disorder appearing later in life when exposed to an adipogenic diet.

The term "adipogenic diet" in the context of the present invention relates to a diet which will lead to increased fat mass of the individual. Generally speaking, an excess of energy intake will lead to increased fat mass, therefore one example of an adipogenic diet is a diet where the caloric intake exceeds the individual's required caloric need. Other examples of an adipogenic diet include the typical Western diet, also known as the western pattern diet or Standard American Diet. Another example of an adipogenic diet is where the diet is characterized by a fat content that exceeds the dietary recommendation of 30% of the energy from fat, high sugar diet and/or that the caloric intake exceeds the individual's required caloric need.

Thus, it is envisaged that the composition for use according to the invention, when administered early in life (for example to an infant not younger than 4 months or young child), will protect that individual if and when said individual later in life (for example as an adult, or for example after 18, after 20, after 25, after 30 years of age) eats a diet which is adipogenic. By protect, it is meant that glucose homeostasis and/or insulin sensitivity will not be impaired, or will be not be impaired to same extent. Without being bound by the theory, it is hypothesised that the use of the composition of the invention, at the time of administration, modulates the metabolic pathways.

In other embodiments, the invention relates to the composition for use according to the invention, wherein the use is to improve insulin sensitivity, to promote normal weight and/or to prevent overweight.

Composition for Use—Target Groups

The composition for use according to the invention is to be administered to an infant not younger than 4 months or to a young child.

In one embodiment the infant or young child is for example born to a mother who herself suffered or suffers from one or more metabolic syndrome disorders, such as one or more selected from the group consisting of diabetes mellitus, impaired glucose tolerance, impaired fasting glucose, insulin resistance, hypertension, dyslipidemia, overweight, obesity (particularly central obesity) and microalbuminuria, or from gestational diabetes.

In a further embodiment the infant or young child is deemed to be at risk for one or more metabolic syndrome disorders, for example due to a familial risk, such as family history, preterm birth, low weight at birth and/or growth restriction.

In one embodiment, the composition for use is to be administered to an infant not younger than 4 months or young child, regardless of birth weight.

In another embodiment of the present invention, the composition for use according to the invention is to be administered to an infant not younger than 4 months, for example 6 months, or young child whose birth weight was normal. In another embodiment the birth weight of the infant or young child was below or above normal.

In a further embodiment, the present invention relates to a composition for use according to the invention, wherein the composition is to be administered to an infant not younger than 4 months, for example 6 months, or young child who underwent a period of catch-up growth following a period of growth restriction.

In a further embodiment, the present invention relates to a composition for use according to the invention, wherein the composition is to be administered to an infant not younger than 4 months, for example 6 months, or young child who has not undergone a period of catch-up growth following a period of growth restriction.

In yet a further embodiment, the present invention relates to a composition for use according to the invention, wherein the composition is to be administered to infant not younger than 4 months, for example 6 months, or young child who was born with normal birth weight and with a non-restricted food intake and normal growth during infancy and/or young age.

Dosage Regimen

The invention relates to the surprising finding that administration of low glycaemic index nutritional compositions to an infant or young child of an age comprised between 4, for example 6, months and 5, for example 2, years can protect from metabolic syndrome disorders later in life.

The complementary composition for use according to the invention is to be administered to the infant or young child in a time period from 4 to 60 months. In other embodiments, the administration falls in a time period from 6 months to 36 months, or 24 months, such as to 18 months, for example to 12 months.

In one embodiment of the present invention, the composition for use according to the invention is administered to an infant or young child during the complementary feeding period.

The complementary feeding period refers to the period in an infant's or young child's life where they are transitioned from exclusive milk feeding (such as breast milk feeding) to mix diet comprising breast milk (or replacers) and solid foods. This period depends on the individual infant or young child, but typically falls within the range from 4 months to 18 months of age, such as from 6 to 18 months.

In one embodiment of the present invention, the complementary composition for use according to the invention is to be administered to an infant or young child of an age comprised between 4 to 60 months and administration should last for at least 3 months, for example 6 months or 9 months or 12 months.

In the above mentioned period administration may be for example intermittent, or for example on average once daily over said the period, or for example once every other day over said period, or for example at least once daily during said period.

In another embodiment of the present invention, the administration of the composition is for a shorter duration of time falling within the time period mentioned above, for example on average once daily for a duration of at least six weeks in said time period; such as for example on average once daily for 3, 6, 8, 9 months during said time period.

Alternatively, the administration may be for example on average once every other day for a period of at least six weeks in the period from 4 months to 60 months, such as for example on average once every other day for a period of 3, 6, 8, or 9 months during said time period.

In other embodiments the invention relates to a use according to the invention, wherein a composition is administered at least once a day for at least 1 month.

In one embodiment of the present invention, the complementary nutritional composition provides to the infant or young child assuming it at least 10%, for example 20%, or 30%, or 50%, or 70%, or 80%, of the total daily caloric intake.

In another embodiment, the complementary nutritional composition provides to the infant or young child assuming the total daily caloric intake.

Nutritional Composition Formats

A medical food is a special class of nutritional composition designed to provide dietary management of certain conditions. The medical food meets certain criteria as set out by and regulated under the Orphan Drug Act of 1983 in Section 5 [360ee](b)(2)(D). The medical food may be presented in any suitable format, as discussed below.

Thus, one embodiment of the invention relates to a complementary nutritional composition according to the invention wherein the nutritional composition is a medical food.

The complementary nutritional composition according to the invention may be in any suitable format.

The format of the complementary nutritional composition for use according to the invention may be tailored to suit the age of the infant or young child to whom it is administered.

Examples of nutritional composition formats suitable for infants include a follow-on formula, a growing up milk, an infant cereal product or a baby food.

Examples of formats suitable for infants and/or young children include ready-to-drink compositions, liquid comestibles, milk drinks, milk-shakes, milk-biscuits, yoghurts, soups, desserts, puddings, bars such as cereal bars, extruded cereals, porridges, beverages and baby foods.

When the complementary nutritional composition is an infant cereal product, it may comprise at least 0.48 g/100 kJ of a protein source, at most 1.1 g/100 kJ of a lipid source and a carbohydrate source.

Infant cereals are known in the art. Infant cereals are compositions containing cereals to be administered to infants. They are usually to be administered using a spoon, and may be offered as dry cereal for infants, for example. Also ready to serve infant cereals are within the scope of the present invention. The codex alimentarius offers guidance on what ingredients an infant cereal should contain. Infant cereals may be intended to be reconstituted either in water or in milk.

Typically, the caloric density as well as the amounts and kinds of proteins, carbohydrates and lipids present in the infant cereal should be carefully adjusted to the needs of the infant and are dependent on the infant stage of development and age.

It is well known that the requirements for nutrition of an infant changes with the development and age of the infant, and the composition of the infant cereal ideally reflects this change.

Hence, a standard infant cereal (to be prepared with milk) according to the present invention to be to be administered to infants at the age of 4-6 months may have an energy density of 220-240 kJ/15 g, 0.8-1.2 g/15.g of a protein source, 0.1-0.3 g of a fat source and 12.3-12.7 g/15.g of a carbohydrate source. Such an infant cereal may contain, for example, Rice flour, Maize Maltodextrin, Vitamin C, and Iron.

A standard infant cereal (to be prepared with milk) according to the present invention to be to be administered to infants at the age of 6-12 months may have an energy density of 220-240 kJ/15 g, 1.5-1.9 g/15 g of a protein source, 0.2-0.4 g of a fat source and 11.1-11.5 g/15 g of a carbohydrate source. Such an infant cereal may contain, for example, Wheat flour, Semolina from wheat, Iron, Vitamin C, Niacin, Vitamin B6, Thiamin, and Maize Maltodextrin.

Hence, an infant cereal to be prepared with water according to the present invention to be administered to infants from the age of 4-6 months may have per 100 g, energy density of 400-420 kcal100g, 10-16 g of a protein source, 7-17 g of a fat source and 50-75 g of a carbohydrate source. Such an infant cereal may contain, for example, Rice flour, Maize Maltodextrin, Vitamin C, and Iron.

An infant cereal according to the present invention to be to be administered to infants at the age of 6-12 months may have an energy Such an infant cereal may contain, for example, Wheat flour, Semolina from wheat, Iron, Vitamin C, Niacin, Vitamin B6, Thiamin, and Maize Maltodextrin.

Infant cereals may be prepared from one or more milled cereals, which may constitute at least 25 weight-% of the final mixture on a dry weight basis.

The infant cereals of the present invention are preferably prepared from a single grain—like rice cereal or wheat cereal—because single grain compositions are less likely to cause an allergic reactions.

Typically, infants cereals are to be mixed with water or milk before consumption. For example 15 g of a infant cereal of the present invention may be to be mixed with 45 mL (complete infant cereal) of water or 90 ml of milk (standard infant cereal) respectively.

Combination of Disclosures

It should be noted that embodiments and features described in the context of one of the aspects of the present invention also apply to the other aspects and embodiments of the invention mutatis mutandis.

The compositions for use according to the invention are herein described by different parameters, such as the ingredients, nutritional composition formats, uses, target groups etc. It should be noted that embodiments, features and exemplary embodiments described in the context of one of the parameters of the composition for use according to the invention, may also be combined with other embodiments, features and exemplary embodiments described in the context of another parameter, unless expressly stated otherwise.

All patent and non-patent references cited in the present application, are hereby incorporated by reference in their entirety.

The invention will now be described in further details in the following non-limiting examples.

Experimental Section

Example 1

The effect of diets during complementary feeding period with different GI on later blood glucose levels during adulthood was investigated, using a rat model of intrauterine growth retardation (IUGR). IUGR model was used as a sensitive model for later impaired glucose homeostasis (see Shankhalili Y. et Al, 2010, *"Comparison of two models on intrauterine growth restriction for early catch up growth and later development of glucose intolerance and obesity in rats"* (Am. J. Physiol Regul Interg Comp Physiol 298; R141-R146).

Study Design:

IUGR was induced in Sprague Dawley (SD) rats by 50% food restriction during last 10 days of gestation. The pups were fed with their dams during suckling period. At the end of suckling period (age 21 d), 40 male pups from the IUGR group and twenty male pups from the Non IUGR group (reference group) were separated from dams.

The IUGR pups were randomly divided into two groups (20/group) with similar body weight and same number of pups from each litter. The pups were then fed ad-libitum from age of 21 to 52 d (phase I) with a modified semi-synthetic AIN96 complementary feeding diet with 15% glucose energy (E) and either 15% galactose E (galactose diet: G IUGR group) or 15% starch E (control diet: C non IUGR and C IUGR groups). The micronutrients and fiber content and macronutrient energy partitioning of both complementary feeding diets were similar with 20% protein E, 17% fat E and 67% CHO E with presence or absence of 15% galactose E as an isocaloric exchange for the corn starch of control diet (Table 1).

Subsequently, all animals were fed ad-libitum with a high fat diet (Kliba 2126, 45% fat E) until age of 155 days (phase II). FIG. 1 shows the design of study.

Food intake and body weight were recorded during the study (2-3 times/week). The baseline blood samples (after 8 hr of food deprivation), were taken from the tail vein at age of 52 and 141 days for glucose and insulin analysis.

A surrogate of glycemic load for rats (SGL) based on a daily intake of 15 g was calculated for the two diets proposed to the groups. For the control diet 20 SGL=7.1 while for the Galactose Diet SGL=5.76, resulting in a 19.2% reduction of SGL relative to the control diet.

TABLE 1

Composition of diets

| Ingredient | Galactose Diet | Control Diet |
| --- | --- | --- |
| Corn flour starch | 33 | 48 |
| K-casein | 20 | 20 |
| D-glucose | 15 | 15 |
| Galactose | 15 | — |
| Soybean oil | 7 | 7 |
| Cellulose | 5 | 5 |
| Mineral Mix | 3.5 | 3.5 |
| Vitamin Mix | 1 | 1 |
| Others | 0.5 | 0.5 |
| Total (wet weight) | 100 | 100 |
| Kcal/100 g wet mixture | 360.0 | 360.0 |
| % Energy | | |
| Protein | 20 | 20 |
| CHO | 62 | 62 |
| Fat | 18 | 18 |

Results
Body Weight and Energy Intake

Figure 2:
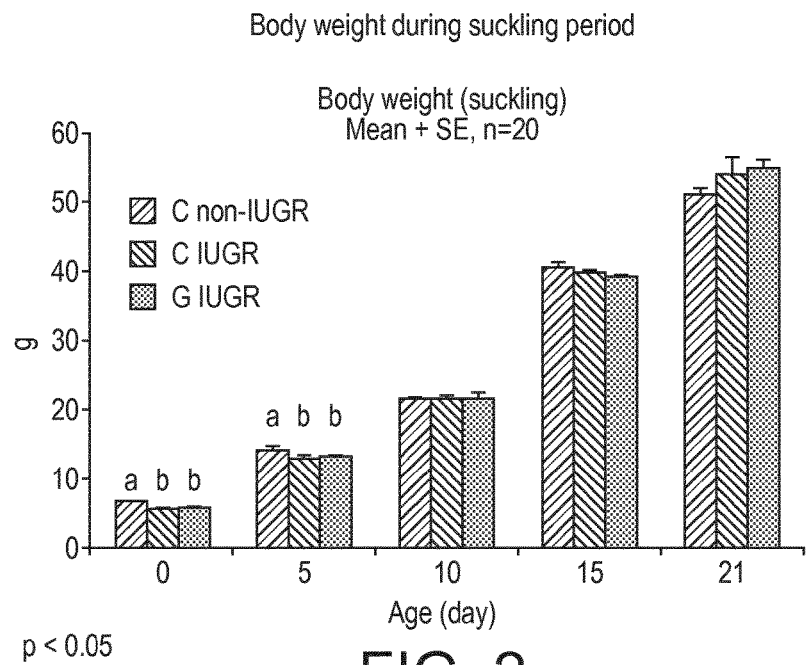
FIG. 2 shows diagram of body weight observed for the different groups of Example 1 from day 0 to day 21.
Figure 3:
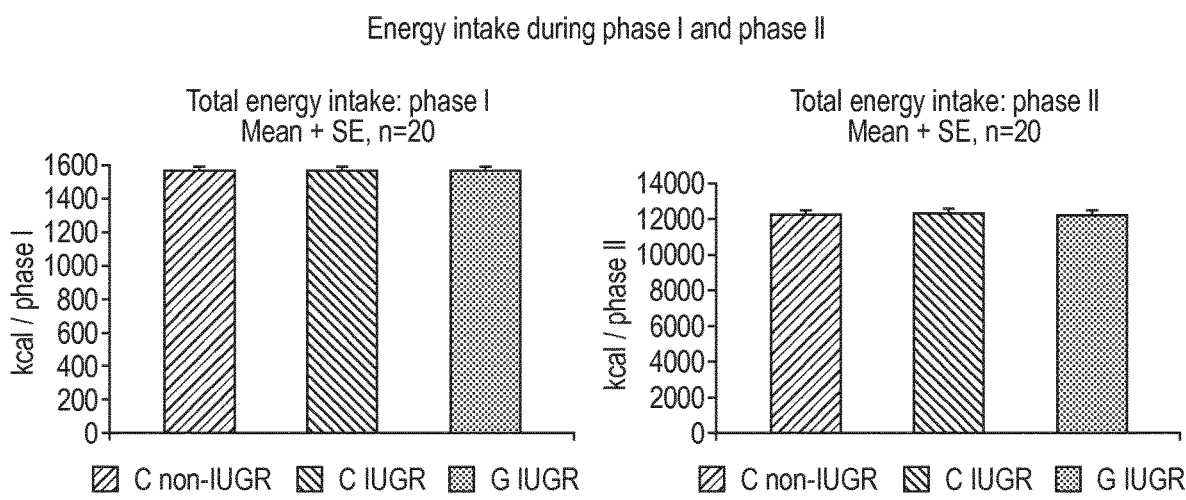
FIG. 3 shows diagrams of energy intake for the three groups of Example 1 during intervention complementary feeding period (Phase I) and follow-up period (Phase II).

Body weight of both IUGR groups was significantly lower than that of non IUGR group at birth. However, IUGR group growth faster than non-IUGR group during first week of suckling period (catch up growth) and all groups had similar body weight from age of 10 days (FIG. 2). Total energy intake (FIG. 3) and body weight (FIG. 4) of all groups were also similar during both the intervention complementary feeding period (phase I) and follow-up period (phase II).

Base Line Blood Glucose and Insulin

The results shows that both IUGR groups had lower blood glucose and insulin baseline relative to non IUGR group at the end of the complementary feeding period (age of 51 days), indicating altered glucose metabolism in IUGR rats and lack of immediate effect of the complementary feeding diet.

Figure 4:
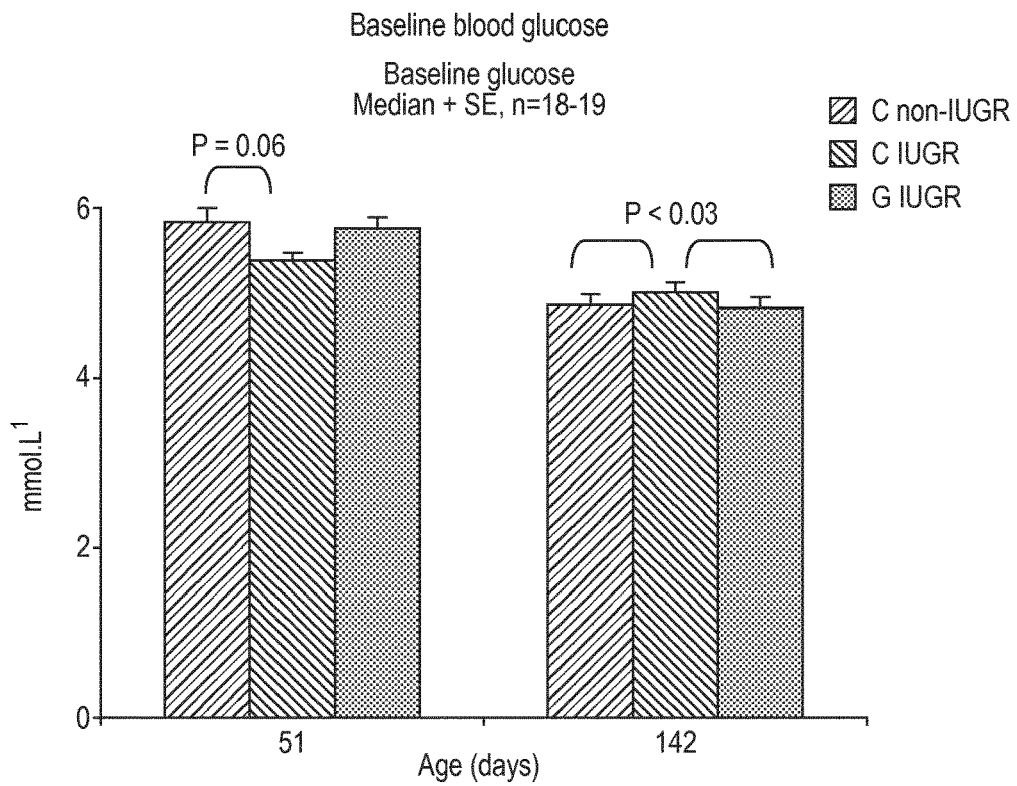
FIG. 4 shows diagrams of baseline blood glucose levels after 8 hours of food deprivation for the three groups in the experiment described Example 1.
Figure 5:
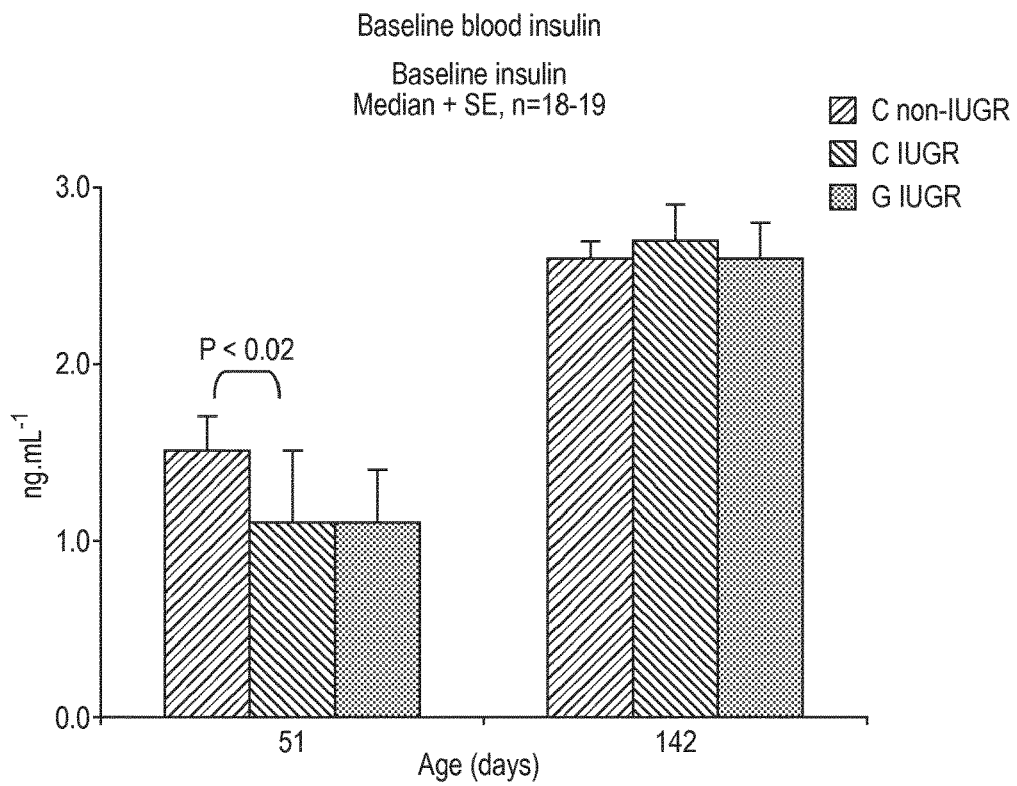
FIG. 5 shows diagrams of baseline blood insulin levels after 8 hours of food deprivation for the three groups in the experiment described in Example 1.

Surprisingly, the IUGR group who was previously fed with galactose (low GI sugar), only during complementary feeding period (age of 21-51 days), had lower blood glucose later at adult age (age of 142 days) relative to control IUGR group who was fed a complementary feeding diet higher in starch content (higher GI carbohydrate) (FIG. 4). The values of the group that received galactose during the complementary period were normalized and resembled those of the reference group non-IUGR. Similar trend was also observed in insulin response at age of 142 days (FIG. 5).

In conclusion, these results shows for the first time that complementary feeding diets with different GI, GL have an impact on later blood glucose/insulin control in the adult age and consequently on the risk of developing metabolic diseases. These findings thus indicate beneficial programming effect of low glycemic load and/or index complementary feeding diets on later control of glucose homeostasis and risk of development of type 2 diabetes and other metabolic diseases later in life.

Example 2

Example of Infant Cereal Product Prepared with Water (% Weight).

A traditional infant cereal product to be reconstituted in water is prepared according to the following recipe: Wheat flour 45% (40.1 g CHO), skim milk 26% (14.6 g CHO), oil 7%, glucose 6%, sucrose 15%, vitamin and minerals 1% The GI (calculated based on ingredient GI) of this example is 70 and GL of 24.6.

Calculation of Glycemic Load (Serving Size of 50 g): GL=24.6

$$[GL = ((40.1/2 \times 71) + (14.6/2 \times 32) + (6.0/2 \times 100) + (15/2 \times 68)/100]$$

A corresponding infant cereal product according to the present invention may be prepared according to the following recipe by using methods known to the person skilled in the art: wheat flour 43% (38.3 g CHO), added lactose 15%, skim milk 26% (14.6 g CHO), oil 13%, sucrose 2%, vitamin and minerals 1%. The GI of this example is 63 and GL of 20.

Calculation of Glycemic Load (Serving Size of 50 g): GL 20=

$$[GL = ((38.3/2 \times 71) + (14.6/2 \times 32) + (15/2 \times 46) + (2/2 \times 68))/100]$$

Example 3

Example of Infant Cereal Prepared with Milk (% Weight).

A traditional infant cereal product to be reconstituted in milk is prepared according to the following recipe: Rice flour 75% (71 g CHO), glucose 7%, sucrose 15%, banana 2% (1.4 g CHO), vitamin and minerals 1%.

Calculation of Glycemic Load (25 g Serving Size): 21—

$$[GL = ((71/4 \times 85) + (7/4 \times 100) + (15/4 \times 68) + (1.4/4 \times 61))/100]$$

A corresponding infant cereal product according to the present invention may be prepared according to the following recipe by using methods known to the person skilled in the art: Rice flour 66% (62.5 g CHO), sucrose 2%, galactose 20%, banana 4% (1,4 g CHO), fat 5%, fiber 2.0%, vitamin and minerals 1%.

Calculation of Glycemic Load (Serving Size of 25 g): 16—

$$[GL = ((62.5/4 \times 71) + (2/4 \times 68) + (20/4 \times 20) + (2.8/4 \times 61))/100]$$

Example 4

Infant Cereal Product to be Prepared with Water (% Weight)

An infant cereal product to be reconstituted in water is prepared according to the following recipe: 23% refined wheat flour with 4% fiber (20 g available CHO with GI 71), 20% whole wheat flour with 8.6% fiber (14 g available CHO with GI 71), 14% red lentils with 11% fiber (8.2 g available CHO with GI 26), 15% Skim milk (8.4 g CHO, GI 32), 12% fat (no GI), 11% sucrose (GI 68), 4% prebiotic (no GI), vitamin and minerals 1% (no GI).(Serving size=50 g powder+150 ml water). Total sugar content:20% w/w
Calculation of Glycemic Load (Serving Size of 50 g): GL=18

$$[GL=((20/2\times71)+(14/2\times71)+(8.2/2\times26)+(8.4/2\times32)+(11/2\times68))/100]$$

Example 5

Infant Cereal Product to be Prepared with Water (% Weight)

An infant cereal product to be reconstituted in water is prepared according to the following recipe: 24% refined wheat flour with 4% fiber (21 g available CHO with GI 71), 15% whole wheat flour with 8.6% fiber (10.5 g available CHO with GI 71), 14% red lentils with 11% fiber (8.2 g available CHO with GI 26), 15% Skim milk (8.4 g CHO, GI 32), 15% fat (no GI), 4% prebiotic (no GI), 4% lactose (GI 46), 8% dried apple with 15% fiber (available CHO of 5.8 with GI 29), vitamin and minerals 1% (no GI) (Serving size=50 g powder+150 ml water). Total sugar content:19% w/w
Calculation of Glycemic Load (Serving Size of 50 g) Provides: GL=15.4

$$[GL=((21/2\times71)+(10.5/2\times71)+(8.2/2\times26)+(8.4/2\times32)+(4/2\times46)+(5.8/2\times29))/100]$$

Reference Example 6

Infant Cereal Product to be Prepared with Water (% Weight)

A traditional infant cereal product to be reconstituted in water is prepared according to the following recipe: 52% refined wheat flour with 4% fiber (43% available CHO with GI 70), 26% skim milk (14.6 g available CHO, GI 36), 6% fat (no GI), 15% sucrose (GI 68), vitamin and minerals 1% (no GI). (Serving size=50 g powder+150 ml water). Total sugar content: 30% w/w.
Calculation of Glycemic Load Provides: GL=22.7

$$GL=((43/2\times71)+(14.6/2\times32)+(15/2\times68))/100$$

Example 7

Infant Cereal Product to be Prepared with Water (% Weight)

An infant cereal product to be reconstituted in water is prepared according to the following recipe: 27% refined wheat flour with 4% fiber (24 g available CHO with GI 71), 20% whole wheat flour with 8.6% fiber (14 g available CHO with GI 71), 14% red lentils with 11% fiber (8.2 g available CHO with GI 26), 15% Skim milk (8.4 g CHO, GI 32), 12% fat (no GI), 11% sucrose (GI 68), vitamin and minerals 1% (no GI).(Serving size=50 g powder +150 ml water). Total sugar content: 20% w/w.
Calculation of Glycemic Load (50 g Serving Size) Provides: GL=19.6

$$[GL=((24/2\times71)+(14/2\times71)+(8.2/2\times26)+(8.4/2\times32)+(11/2\times68))/100]$$

Example 8

Infant Cereal Product to be Prepared with Water (% Weight)

An infant cereal product to be reconstituted in water is prepared according to the following recipe: 28% refined wheat flour with 4% fiber (25 g available CHO with GI 71), 15% whole wheat flour with 8.6% fiber (10.5 g available CHO with GI 71), 14% red lentils with 11% fiber (8.2 g available CHO with GI 26), 15% Skim milk (8.4 g CHO, GI 32), 15% fat (no GI), 4% lactose (GI 46), 8% dried apple with 15% fiber (available CHO of 5.8, GI 29), vitamin and minerals 1% (no GI) (Serving size=50 g powder+150 ml water). Total sugar content: 19% w/w.
Calculation of Glycemic Load Provides: GL=16.8

$$[GL=((25/2\times71)+(10.5/2\times71)+(8.2/2\times26)+(8.4/2\times32)+(4/2\times46)+(5.8/2\times29))/100]$$

Although due to species differences SGL and GL differ in their absolute values, it is to be noted that the decrease in GL results in a 18.5% and 33% reduction when comparing Reference Example 6 to, respectively, Example 4 and 5. This thus shows reduction in GL at least comparable to what observed in rats with SGL when moving from traditional products to products according to the invention.

Example 9

Two complete infant cereals compositions according to the present invention (Prototype) and Prototype 2) were compared in a clinical trial to a Reference existing complete infant cereal product.

The study design was a randomized, single center, double blind, crossover, with three test meals (reference existing infant cereal and 2 infant cereal prototypes). Table 2 below shows the composition of infant cereal products.

TABLE 2

| Main macronutrient composition of tested infant cereals (g/100 g power) | | | |
|---|---|---|---|
| | Reference | Prototype 1 | Prototype 2 |
| Wheat refined flour (starch) | 40.5 | 16 | 15.5 |
| Wheat whole grain starch | | 19.9 | 14.7 |
| Glucose & maltose | 20.5 | 8.0 | 8.3 |
| sucrose | | 11.0 | |
| isomaltulose | | | 5.0 |
| Red lentil | | 14.0 | 14.0 |
| Skim milk | 27.0 | 14.8 | 14.4 |
| (of which lactose) | (15.1) | (8.2) | (8.0) |
| Added fibre | | 4.0 | 4.0 |
| Added Fat | 9.0 | 12.0 | 15.3 |
| Dried Fruit* | | | 8.0 |
| Added fructose | 2.7 | | |
| GL (50 g serving) | 26 | 20 | 17 |

*2.1 g sucrose & 3.6 g fructose

Total sugar content (including milk lactose and fruit sugars) of tested meals are; 38% in Reference diet, 27.3% in prototype 1 and 27% in prototype 2.

20 healthy men of 21-45 years old with BMI of 22.3±2.03 Kg/m2, consumed all 3 study infant cereals, after an overnight fasting, in a random order with at least 3 days interval between tests. The study was performed as per international standard ISO 26642, 2010.10.01 for glycemic index. The study meals were prepared with 75 g infant cereal powder diluted with 225 ml of pre-boiled lukewarm water (40° C.) and consumed within 10 minutes together with 250 ml water. Finger picked capillary blood samples were taken at fasting (−10 & 0 minutes before test meals) and following 15, 30, 45, 60, 90, 120, 150 and 180 minutes after start of test meals intake.

Capillary blood glucose was analyzed by Cobas, using Roche GLUC2 (04657527, Switzerland). Serum insulin was analyzed by AlphaLISA® Human Insulin Immunoassay Kit, PerkinElmer Inc.

Figure 6:
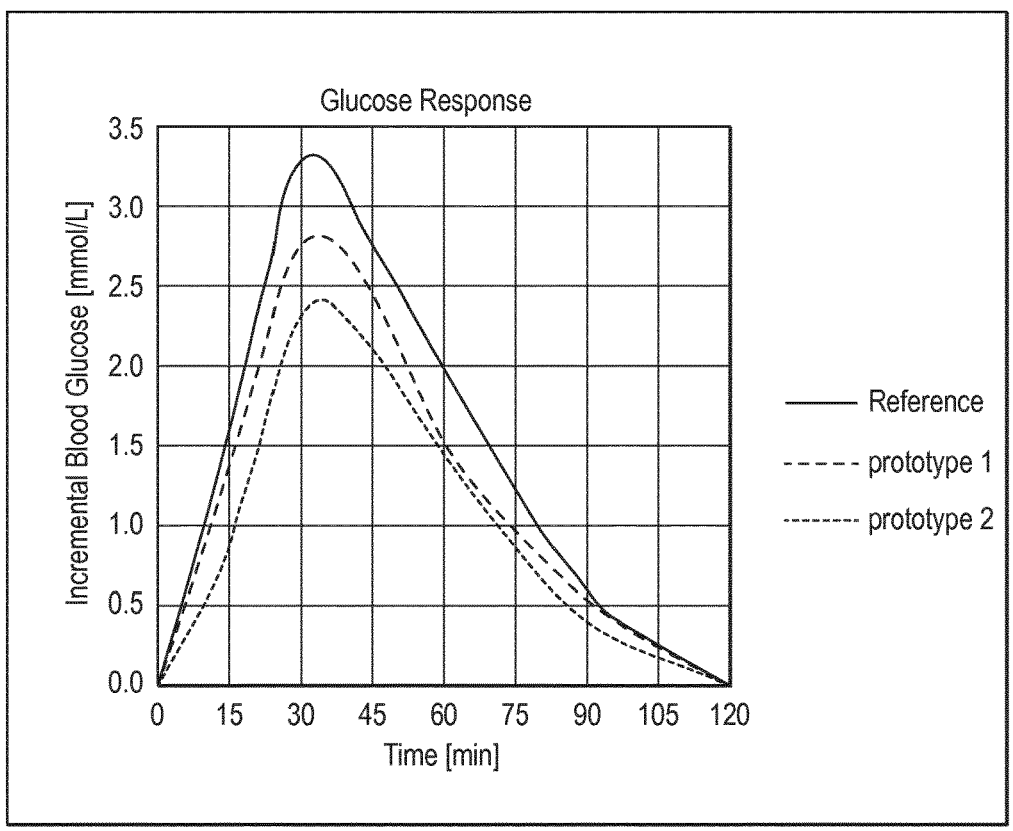
FIG. 6 shows postprandial increase in glucose in response to the products tested in Example 9.
Figure 7:
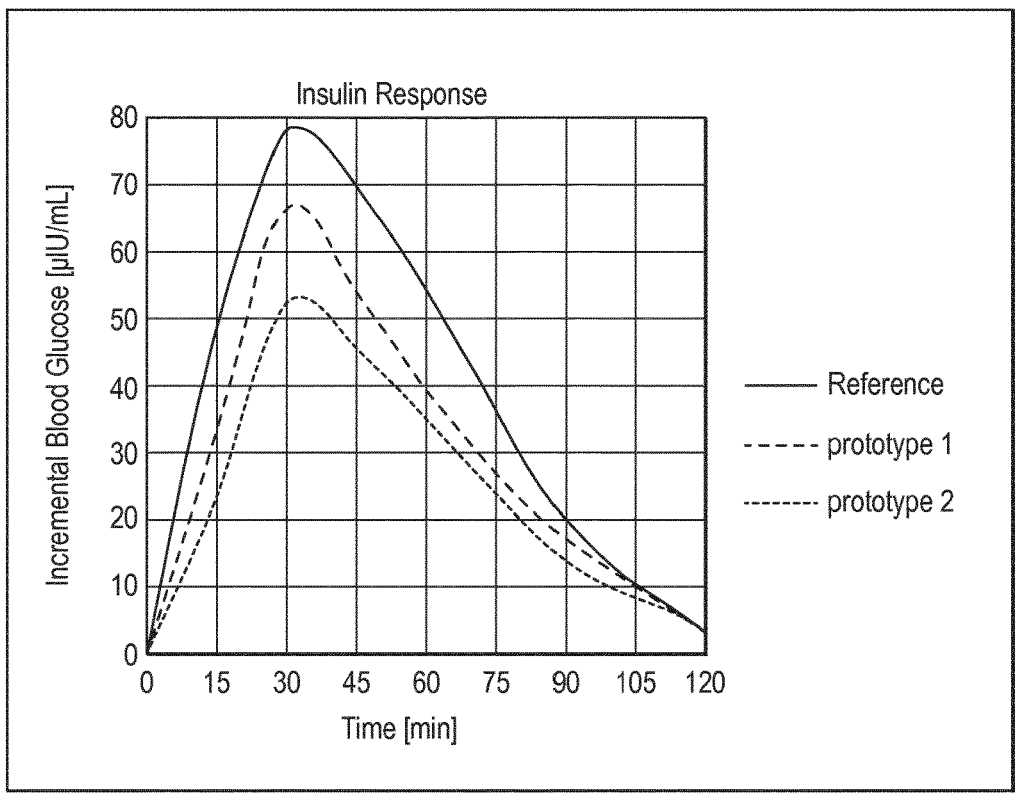
FIG. 7 shows the postprandial increase in insulin in response to the products tested in Example 9.
Figure 8:
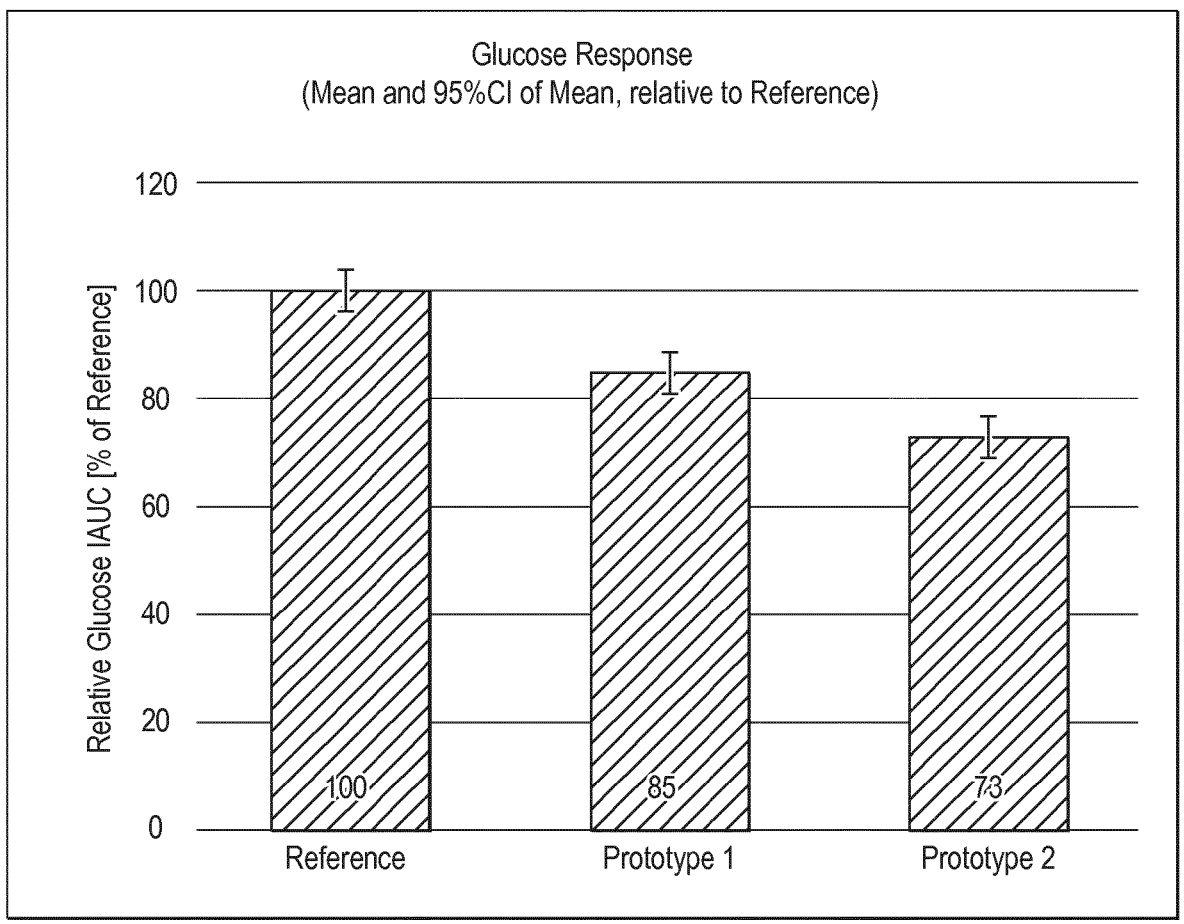
FIG. 8 shows glucose incremental area under the curve (IAUC) of prototypes 1 and 2 of Example 7 relative to glucose IAUC of Reference product from the same example.
Figure 9:
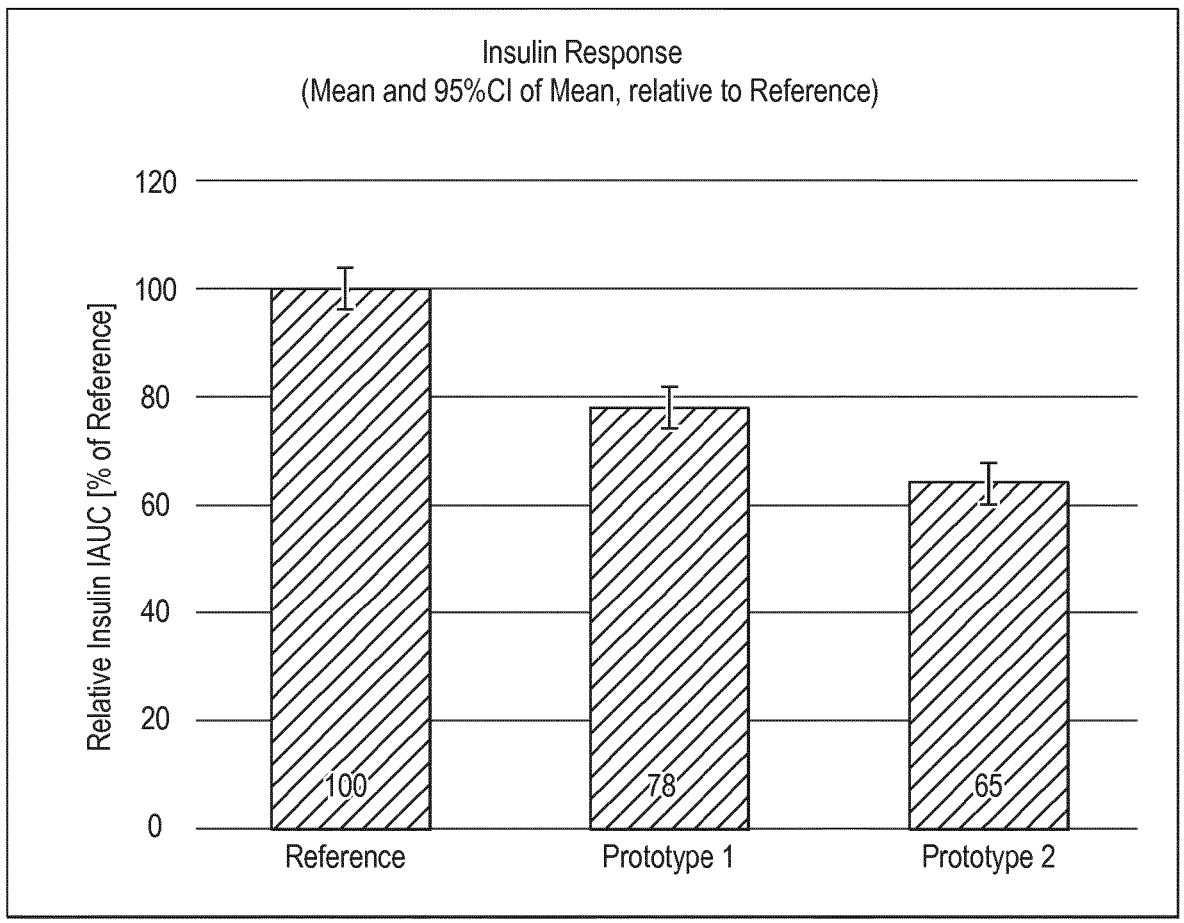
FIG. 9 shows insulin IAUC of prototypes 1 and 2 of Example 9 relative to insulin IAUC of Reference product from the same example. Detailed description of the invention

The postprandial 2 hours incremental area under curve (IAUC) of glucose and insulin were calculated using the trapezoidal rule. Results of postprandial increase in glucose and insulin responses are presented FIGS. 6-7 and 2-hr IAUC relative to Reference in FIGS. 8-9.

The results of the clinical trial clearly demonstrate the benefit of reformulated infant cereal prototypes (having low of GL 20 and 17 respectively) in lowering both postprandial glucose and insulin responses relative to the Reference product (having high GL of 26).

Relative to the Reference product, the 2-hr glucose and insulin IAUC were 15% and 22% lower in response to the Prototype 1 and 25% and 35% lower in response to the Prototype 2, respectively ($p<0.05$ in all cases).

The invention claimed is:

1. A method for treatment, prevention and/or reducing a risk of a metabolic syndrome disorder appearing later in life in a young child born to a mother who suffered or suffers from a metabolic syndrome disorder, the method comprising administering to the young child a complementary nutritional composition with a low glycaemic load, the complementary nutritional composition comprising
   cereal flour in an amount ranging from 20 to 90% w/w of the complementary nutritional composition,
   legumes in an amount ranging from 5 to 40% w/w of the complementary nutritional composition, and
   fruits in an amount ranging from 1 to 25% w/w of the complementary nutritional composition, and
   the young child is an age between 12 months and 5 years.

2. The method according to claim 1, wherein the complementary nutritional composition has a low glycemic index and/or comprises an ingredient having a low glycemic index.

3. The method according to claim 1, wherein the complementary nutritional composition comprises at least one carbohydrate-based ingredient with a low glycemic index.

4. The method according to claim 3, wherein the carbohydrate-based ingredient with the low glycemic index is selected from the group consisting of sucrose, lactose, isomaltulose, galactose, fructose, and mixtures thereof.

5. The method according to claim 1, wherein the complementary nutritional composition has a fat content ranging from 8 to 20% w/w of the complementary nutritional composition.

6. The method according to claim 1, wherein the complementary nutritional composition comprises added sugars with a low glycemic index in an amount ranging from 1 to 20% w/w of the complementary nutritional composition.

7. The method according to claim 1, wherein the complementary nutritional composition comprises added fibers in an amount ranging from 1 to 8% w/w of the complementary nutritional composition.

8. The method according to claim 1, wherein the complementary nutritional composition comprises a milk-based ingredient in an amount ranging 1 to 25% w/w of the complementary nutritional composition.

9. The method according to claim 1, wherein the complementary nutritional composition comprises the legumes in an amount ranging from 8 to 30% w/w of the complementary nutritional composition.

10. The method according to claim 1, wherein the complementary nutritional composition comprises the fruits in an amount ranging from 1 to 15% w/w of the complementary nutritional composition.

11. The method according to claim 1, wherein the young child is at risk of developing a metabolic syndrome disorder.

12. The method according to claim 1, wherein the complementary nutritional composition is a principal feeding source for the young child.

13. The method according to claim 1, wherein the complementary nutritional composition comprises the cereal flour in an amount ranging from 30 to 55% w/w of the complementary nutritional composition.

14. The method according to claim 1, wherein the complementary nutritional composition comprises the legumes in an amount ranging from 10 to 25% w/w of the complementary nutritional composition.

15. The method according to claim 1, wherein the complementary nutritional composition comprises the fruits in an amount ranging from 1 to 18% w/w of the complementary nutritional composition.

16. The method according to claim 1, wherein the low glycemic load is a glycemic load equal to or lower than 20.

17. The method according to claim 2, wherein the low glycemic index is a glycemic index equal to or lower than 70.

18. The method according to claim 3, wherein the low glycemic index is a glycemic index equal to or lower than 70.

* * * * *